(12) United States Patent
Takada et al.

(10) Patent No.: US 8,685,403 B2
(45) Date of Patent: Apr. 1, 2014

(54) INSULIN-LIKE GROWTH FACTOR SIGNALING AND INTEGRIN

(75) Inventors: Yoshikazu Takada, Davis, CA (US); Jun Saegusa, Kobe (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/146,907

(22) PCT Filed: Jan. 29, 2010

(86) PCT No.: PCT/US2010/022561
§ 371 (c)(1),
(2), (4) Date: Nov. 15, 2011

(87) PCT Pub. No.: WO2010/088502
PCT Pub. Date: Aug. 5, 2010

(65) Prior Publication Data
US 2012/0082675 A1 Apr. 5, 2012

Related U.S. Application Data

(60) Provisional application No. 61/148,837, filed on Jan. 30, 2009.

(51) Int. Cl.
*A61K 39/00* (2006.01)
*C07K 14/00* (2006.01)

(52) U.S. Cl.
USPC ..... 424/184.1; 424/185.1; 514/1.1; 514/19.2; 514/21.2; 530/350

(58) Field of Classification Search
None
See application file for complete search history.

(56) References Cited

U.S. PATENT DOCUMENTS

| 8,343,918 | B2 * | 1/2013 | Glass et al. | 514/8.6 |
| 2005/0288217 | A1 | 12/2005 | Clemmons et al. | |
| 2006/0166328 | A1 | 7/2006 | Glass et al. | |
| 2008/0199479 | A1 | 8/2008 | Stitt et al. | |

OTHER PUBLICATIONS

Zhang et al. Positively charged side chains in the insulin-like growth factor-1 C- and D-regions determine receptor binding specificity. J. Biol. Chem. 269, 10609-10613, 1994.*
Jansson et al. The insulin-like growth factor (IGF)binding protein 1 binding epitope on IGF-I probed by heteronuclear NMR spectroscopy and mutational analysis.. J Biol Chem. Sep. 18, 1998;273(38):24701-7.*
Epa et al. Model for the complex between the insulin-like growth factor I and its receptor: towards designing antagonists for the IGF-1 receptor. Protein Engineering, Desing & Selection 19(8):377-384, 2006.*
Lou et al The first three domains of the insulin receptor differ structurally from the insulin-like growth factor 1 receptor in the regions governing ligand specificity. PNAS, 103(33):12429-12434, 2006.*
Amino acids. http://sbrs.cm.utexas.edu/WS/aa.pdf, p. 1, Jan. 9, 2013.*
International Search Report dated Jul. 29, 2010, issued in related International Patent Application No. PCT/US2010/022561, filed Jan. 29, 2010.
Aumailley et al., "Arg-Gly-Asp constrained within cyclic pentapeptides. Strong and selective inhibitors of cell adhesion to vitronectin and laminin fragment P1," 1991, Febs. Lett. , 291(1); 50-54.
Bikle et al., "Integrins, insulin like growth factors, and the skeletal response to load," 2008, Osteoporos. Int., vol. 19, pp. 1237-1246.
Dunn et al., "A Dominant Negative Mutant of the Insulin-like Growth Factor-I Receptor Inhibits the Adhesion, Invasion, and Metastasis of Breast Cancer," 1998, Cancer Res., 58(15); 3353-3361.
Oh et al., "Characterization of the affinities of insulin-like growth factor (IGF)- binding proteins 1-4 for IGF-I, IGF-II, IGF-I/insulin hybrid, and IGF-I analogs," 1993, Endocrinol., 132(3); 1337-1344.
Saegusa et al., "The Direct Binding of Insulin-like Growth Factor-1 (IGF-1) to Integrin $\alpha v\beta 3$ Is Involved in IGF-1 Signaling," 2009, J. Biol. Chem., 284, 24106-24114.
Shaw et al., "Integrin Function in Breast Carcinoma Progression," Annual Report prepared for U.S. Army Medical Research and Material Command, Fort Detrick, MD.; Nov. 20, 2000. pp. 46-73 [online]; downloaded from http://www.dtic.mil/cgib-in/getTRDoc?AD=ADA383962&Location=U2&doc=getTRDoc.pdf on Jul. 22, 2010.

* cited by examiner

*Primary Examiner* — Maher Haddad
(74) *Attorney, Agent, or Firm* — Kilpatrick Townsend & Stockton LLP

(57) ABSTRACT

Interaction between insulin-like growth factor 1 (IGFI) and integrin is involved in integrin-mediated cellular signaling, such as enhanced proliferation of cells expressing integrins, especially integrin alpha v beta 3, alpha 6 beta. 1 and alpha 6. beta. 4. A method for inhibiting integrin signaling by using an inhibitor of IGFI-integrin binding is disclosed A method for identifying inhibitors of IGFI-integrin binding is also described. Further disclosed are polypeptides, nucleic acids, and corresponding compositions for inhibiting integrin signaling.

10 Claims, 21 Drawing Sheets

Fig. 6a  NIH3T3-IGF1R
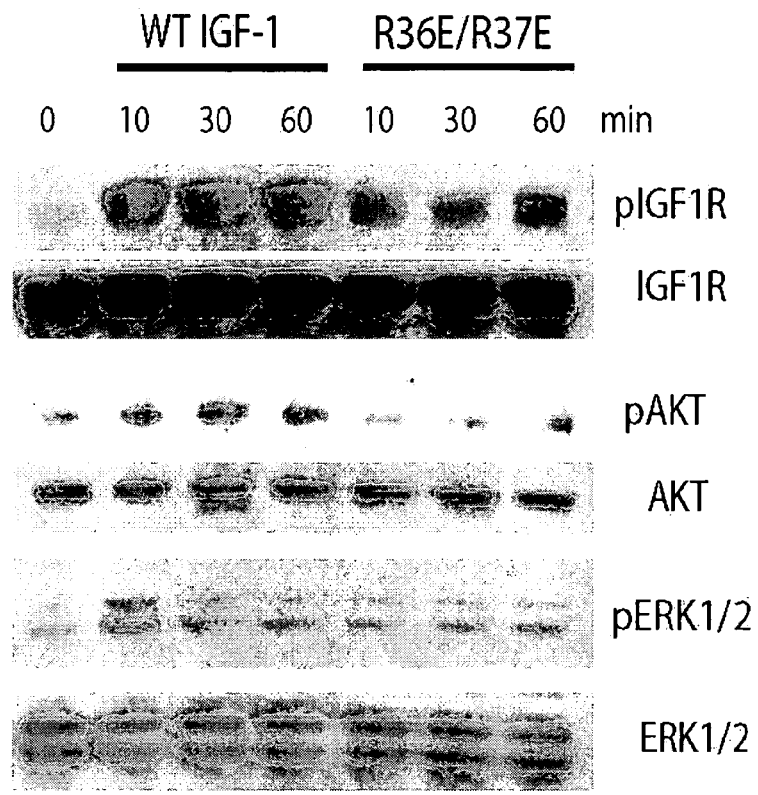
Fig. 6b  C2C12
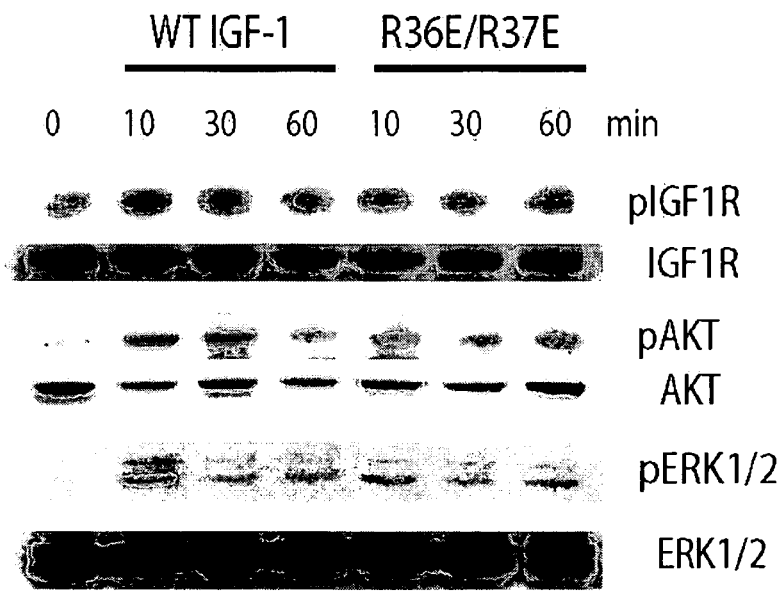

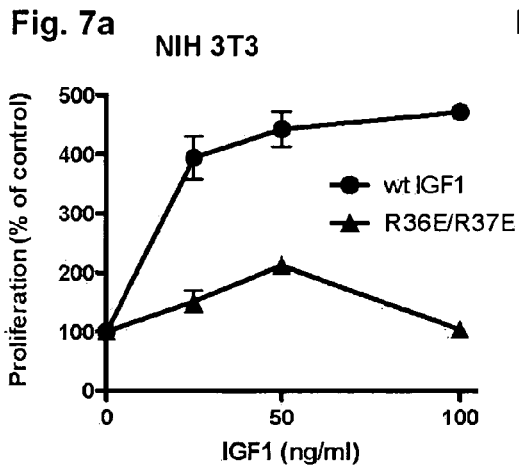
Fig. 7a NIH 3T3
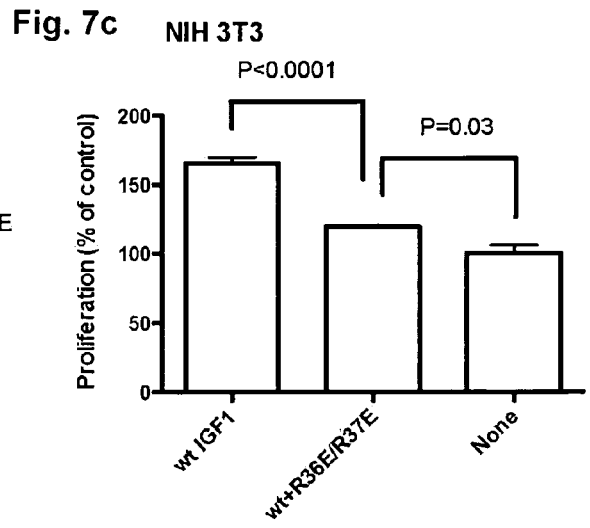
Fig. 7c NIH 3T3
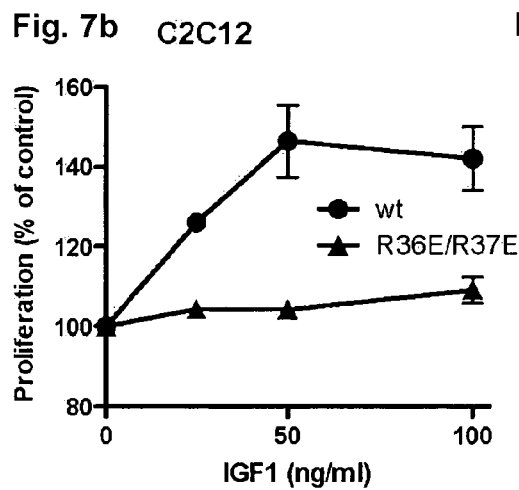
Fig. 7b C2C12
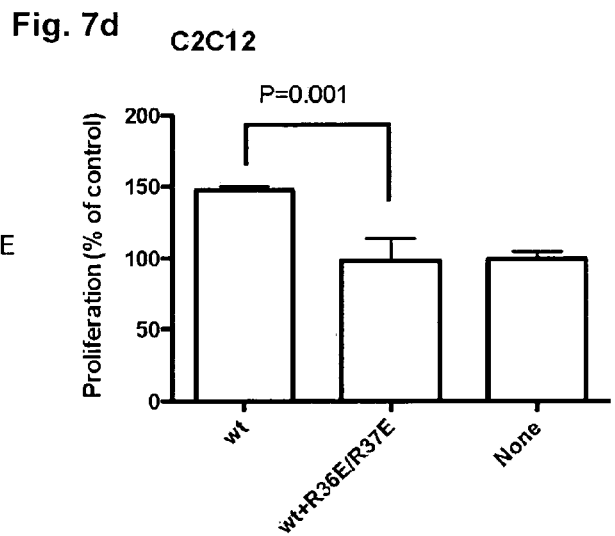
Fig. 7d C2C12

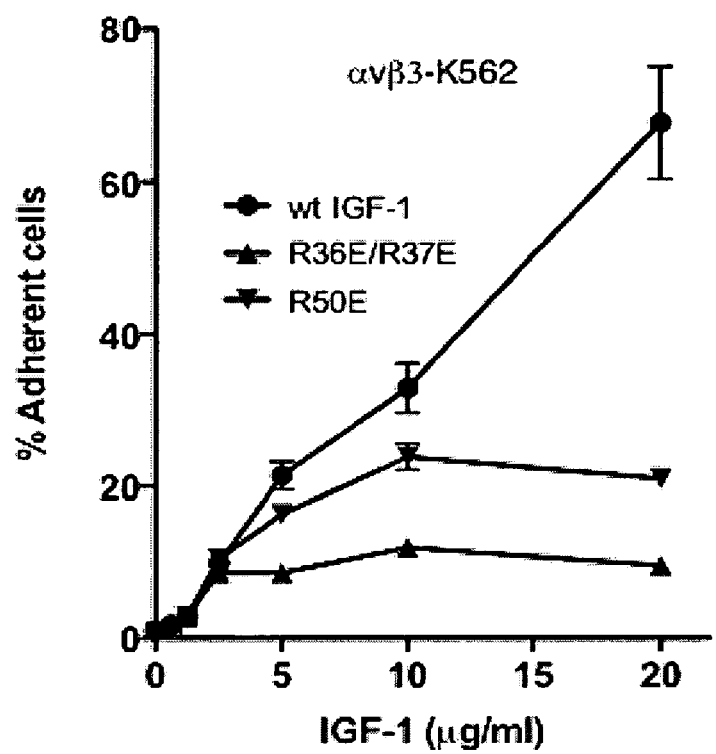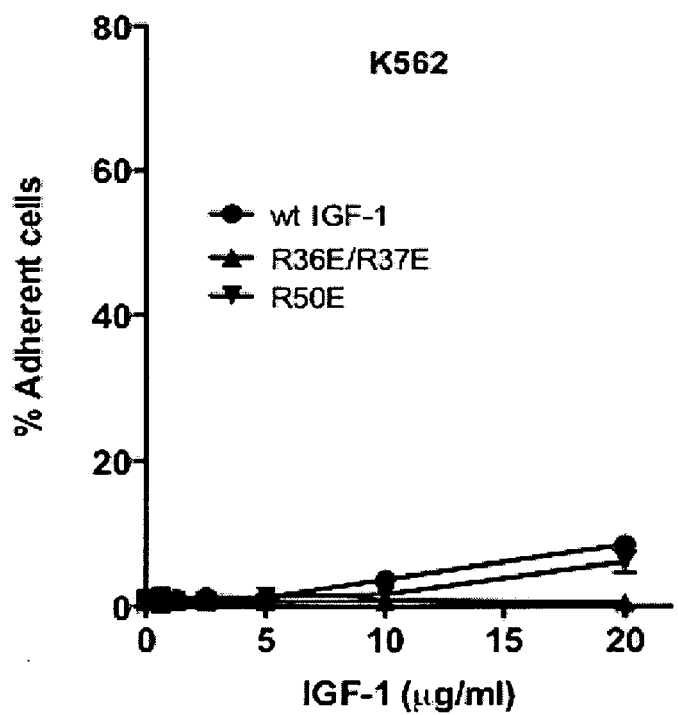
Fig. 12

INSULIN-LIKE GROWTH FACTOR SIGNALING AND INTEGRIN

CROSS-REFERENCES TO RELATED APPLICATIONS

This application is the U.S. National Stage entry under §371 of International Application No. PCT/US2010/022561, filed Jan. 29, 2010, which claims the benefit under 35 U.S.C. §1.119(e) of U.S. provisional Application No. 61/148,837, filed Jan. 30, 2009 the contents of which are incorporated by reference in their entirety.

STATEMENT AS TO RIGHTS TO INVENTIONS MADE UNDER FEDERALLY SPONSORED RESEARCH AND DEVELOPMENT

This invention was made with Government support under Grant No. 5U19CA113298-040002 by the National Institutes of Health and the National Cancer Institute. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-1961-2.TXT, created on Sep. 27, 2012, 8,192 bytes, machine format IBM-PC, MS-Windows operating system, is hereby incorporated by reference in its entirety for all purposes.

BACKGROUND OF THE INVENTION

Integrins are a family of cell adhesion receptors that mediate cell-extracellular matrix interaction and cell-cell interaction (Hynes, Cell 110(6): 673-87, 2002). It has been proposed that signaling from inside cells regulates the ligand-binding affinity of integrins (inside-out signaling) (Shattil, Trends Cell Biol 15(8): 399-403, 2005). Each integrin is a heterodimer containing α and β subunits. At present 18 α and 8 β subunits have been identified, which combine to form 24 integrins (Takada et al., Genome Biol 8(5): 215, 2007).

It has been reported that integrin αvβ3 plays a role in cancer proliferation and invasiveness. High levels of integrin αvβ3 correlate with growth and/or progression of melanoma (Albelda, EXS 61: 188-192, 1992; Hsu et al., Am J Pathol 153(5): 1435-42, 1998) neuroblastoma (Gladson et al., Am J Pathol 148(5): 1423-34, 1996), breast cancer (Pignatelli et al., Hum Pathol 23(10): 1159-66, 1992; Sengupta et al., J Exp Clin Cancer Res 20(4): 585-90, 2001), colon cancer (Vonlaufen et al., Mod Pathol 14(11): 1126-32, 2001), ovarian cancer (Liapis et al., Diagn Mol Pathol 5(2): 127-35, 1996), and cervical cancer (Chattopadhyay and Chatterjee, J Exp Clin Cancer Res 20(2): 269-75, 2001). Moreover, individuals homozygous for the β3L33P polymorphism that enhances the affinity of β3 integrins have an increased risk to develop breast cancer, ovarian cancer, and melanoma (Bojesen et al., Endocr Relat Cancer 12(4): 945-52, 2005). It remains unclear, however, if and how increased levels of αvβ3 on tumor cells contribute to cancer development.

Insulin-like growth factor-1 (IGF1) is a polypeptide hormone (75-kD) that has a high degree of structural similarity to human proinsulin. IGF1 acts through binding to the type I IGF receptor (IGF-IR), a receptor tyrosine kinase. The IGF-IR is a heterotetramer that consists of two α-subunits, which contain the ligand binding domains, and two β-subunits, which possess the tyrosine kinase activity. After ligand binding, the receptor undergoes a conformational change resulting in the activation of the tyrosine kinase, which leads to transphosphorylation of the opposite β-subunit on specific tyrosine residues. These phosphotyrosines then bind to adaptor molecules such as Shc and IRS-1. Phosphorylation of these proteins leads to activation of the phosphatidylinositol 3-kinase (PI3K) and mitogen-activated protein kinase (MAPK) signaling pathways (reviewed in Clemmons and Maile, Mol Endocrinol 19(1): 1-11, 2005).

IGF1 has been implicated in cancer progression (Clemmons et al., Growth Horm IGF Res 17(4): 265-70, 2007). One of the major actions of IGF1 is to inhibit apoptosis. IGF1 confers resistance to chemotherapy and radiation therapy. IGF1 expression levels are increased in breast, lung, prostate, and many other cancers. Several strategies to target IGF1 signaling have been extensively studied, including siRNA or monoclonal antibodies for IGF-IR and kinase inhibitors to inhibit the enzymatic activity of the receptor. The IGF1 system is a therapeutic target for cancer, and elucidation of the IGF1 signaling pathway should have a major impact in designing new therapeutic strategies.

It has been proposed that ligand occupancy of αvβ3 with extracellular matrix ligands such as vitronectin plays a critical role in enhancing IGF1 signaling (Clemmons et al., Growth Horm IGF Res 17(4): 265-70, 2007). It has been reported that inhibiting αvβ3-extracellular matrix interaction ("ligand occupancy") of αvβ3 inhibited IGF1 actions selectively in cell types that express αvβ3 (Clemmons et al., Growth Horm IGF Res 17(4): 265-70, 2007). Inhibiting "ligand occupancy" of αvβ3 has been reported to block IGF1 induced cell migration (Jones et al., Prog Growth Factor Res 6(2-4): 319-27, 1995), DNA synthesis, IRS-1 phosphorylation, and IGF-1R-linked down stream signaling events, such as activation of PI3K and ERK1/2 (Zheng and Clemmons, Proc Natl Acad Sci USA 95(19): 11217-22, 1998).

The present inventors have demonstrated that expression of αvβ3 enhances proliferation of ovarian cancer cells in the presence of fetal bovine serum (FBS) and in serum-free conditions if IGF1 is present. This indicates that IGF1 is involved in enhanced proliferation of αvβ3-expressing cells. The inventors have demonstrated that αvβ3 binds to IGF1 in several different binding assays. It has been found that three Arg residues at positions 36, 37, and 50 in the C-domain of IGF1 are critical for integrin binding by docking simulation and mutagenesis. Mutation of one or more of these Arg residues to Glu (the R36E/R37E or R50E mutation) effectively reduces integrin binding. Interestingly, the R36E/R37E mutant is defective in inducing cell proliferation and IGF1 intracellular signaling while they still bind to IGF1R. These results suggest that the direct binding to IGF1 plays a role in IGF1 signaling. Notably, the inventors demonstrated that the R36E/R37E mutant as well as the R50E mutant suppressed cell proliferation induced by wild type IGF1, suggesting that these mutants are so-called dominant-negative mutants. Taken together, this discovery indicates that the direct binding of αvβ3 to IGF1 plays a role in IGF1 signaling.

Thus, an IGF1 mutant that does not trigger IGF1 signaling while retaining its ability to bind IGF1R (such as the mutants created by the present inventors) has an immediate utility as a therapeutic in conditions involving inappropriate cellular proliferation, e.g., various forms of cancer. Also, these mutants are a powerful tool for studying the role of integrins in IGF1 signaling. Furthermore, the integrin-binding site within the C-domain of IGF1 provides a valuable tool for identification of additional inhibitors of IGF1-integrin binding, as these inhibitors can be useful in cancer therapy.

Because of the prevalence of cancers, there remains a need to develop new strategies for cancer treatment. The present invention addresses this and other related needs.

BRIEF SUMMARY OF THE INVENTION

This invention provides new methods and compositions useful for inhibiting IGF1 signaling in a cell, based on the surprising discovery that the interaction between IGF1 and certain integrin molecules is involved in IGF1-mediated signaling. Thus, in one aspect, the present invention relates to a method for inhibiting IGF1 signaling in a cell, comprising the step of contacting the cell with an effective amount of an inhibitor of IGF1-integrin binding.

In some embodiments, the integrin is $\alpha v\beta 3$. In some embodiments, the integrin is $\alpha 6\beta 1$. In some embodiments, the integrin is $\alpha 6\beta 4$. In some embodiments, the inhibitor is a dominant-negative IGF1 mutant. In other embodiments, the inhibitor is IGF1 mutant R36E/R37E, or R50E. In other embodiments, the inhibitor is anti-$\beta 3$ mAb 7E3, an anti-$\alpha 6\beta 1$ antibody, and anti-$\alpha 6\beta 4$ antibody, or cyclic RGDfV peptide. In some embodiments, the cell is within a patient's body. In other embodiments, the contacting step is performed by intravenous, intraperitoneal, or intratumor injection.

In a second aspect, the present invention relates to a method for identifying an inhibitor of IGF1-integrin binding. This method comprises the following steps: (1) contacting an integrin and a polypeptide comprising an integrin-binding sequence of an IGF1, in the presence of a test compound, and under conditions permissible for IGF1-integrin binding; and (2) detecting the level of polypeptide-integrin binding, wherein a decrease in the level of binding when compared with the level of binding in the absence of the test compound indicates the compound as an inhibitor of IGF1-integrin binding.

In some embodiments, the integrin is $\alpha v\beta 3$. In some embodiments, the integrin is $\alpha 6\beta 1$. In some embodiments, the integrin is $\alpha 6\beta 4$. In other embodiments, the polypeptide comprises the C-domain of IGF1 or the entire length of IGF1. In some cases, the polypeptide further comprises a heterologous amino acid sequence, for example, a glutathione S-transferase (GST). In some embodiments, the polypeptide is expressed on a cell surface.

In a third aspect, the present invention relates to an isolated polypeptide comprising an amino acid sequence that (1) has at least 95% sequence identity to the sequence of a naturally occurring wild-type IGF1 protein, such as a wild-type human IGF1 protein; (2) comprises substitutions of at least one of three Arg residues at positions 36, 37, and 50 of a wild type human IGF1 protein; and (3) inhibits IGF1-integrin binding. The invention also relates to an isolated nucleic acid encoding this polypeptide, as well as a recombinant expression cassette comprising the nucleic acid or an isolated host cell comprising such a recombinant expression cassette.

In some embodiments, the integrin is $\alpha v\beta 3$. In some embodiments, the integrin is $\alpha 6\beta 1$. In some embodiments, the integrin is $\alpha 6\beta 4$. In some embodiments, the Arg residues at positions 36 and 37 but not 50 are substituted. In other embodiments, the Arg residue at position 50 is substituted. In some cases, each of the Arg residues is substituted with a Glu residue.

In a fourth aspect, the present invention relates to a composition comprising (A) a physiologically acceptable excipient and (B) a polypeptide comprising an amino acid sequence that (1) has at least 95% sequence identity to the sequence of a naturally occurring wild-type IGF1 protein, especially a wild-type human IGF1 protein; (2) comprises substitutions of at least one of three Arg residues at positions 36, 37, and 50 of a wild-type human IGF1 protein; and (3) inhibits IGF1-integrin binding. The invention also relates to a composition comprising a nucleic acid encoding the polypeptide described above with a pharmaceutically acceptable excipient.

In some embodiments, the polypeptide is IGF1 mutant R36E/R37E or R50E.

In a fifth aspect, the present invention provides a kit for inhibiting IGF1 signaling. The kit includes the composition of a polypeptide or nucleic acid as described above with a pharmaceutically acceptable excipient. Instruction manual or user information in other forms is generally included in the kit.

***P<0.0001 compared to purified mouse IgG. c) Binding of purified soluble αvβ3 to IGF1. Wells of 96-well microtiter plate were coated with IGF1 and incubated with recombinant soluble αvβ3 (5 µg/ml) in the presence of 1 mM MnCl$_2$ for 1 h at room temperature. Bound αvβ3 was determined using anti-β3 mAb and peroxidase-labeled anti-mouse IgG. Data is shown as means+/−SEM of triplicate experiments. d)-e) CHO cells that express α6β1 or α6β4 adhere to immobilized wt IGF1. Wt IGF1 was immobilized to wells of 96 well-microtiter plates at 0-40 µg/ml coating concentrations. Remaining protein binding sites were blocked with BSA. CHO cells that express recombinant αvβ3 (β3-CHO), β1 (β1-CHO), α6β1 (α6β1-CHO) or α6β4 (α6β4-CHO) were incubated with in the wells for 1 h at 37 C. Bound cells were measured after gentry rinsing the wells. The results suggest that IGF1 binds to integrins other than αvβ3. It was observed that R36E/R37E IGF1 did not interact with α6β1 or α6β4 (*P<0.05). Since α6β4 is involved in tumor progression and migration, this interaction is relevant in cancer.

Figure 4:

FIG. 4 Docking simulation of IGF1-αvβ3 interaction. a. A model of IGF1-integrin interaction. Docking simulation of the interaction between IGF1 (Chain I of PDB code 1WQJ, the IGF1-IGFBP4 complex) and integrin αvβ3 (PDB code 1L5G) was performed as described in the Methods section using AutoDock3. The headpiece of 1L5G was used as a receptor. The pose in the cluster 1 with the lowest docking energy −19.46 Kcal/mol is shown. This pose represents the most stable pose of 1GF1 when IGF1 interacts with integrin αvβ3. b. Positions of amino acid residues that are selected for mutagenesis at the predicted interface between IGF1 and αvβ3. Arginine residues at positions 36 and 37 within the predicted integrin-binding site in IGF1 were selected for mutagenesis.

FIG. 5 Localization of the integrin-binding site in IGF1. a and b) The R36E/R37E mutant did not support the adhesion of K562 cells that express integrin αvβ3. Wells of 96-well microtiter plate were coated with IGF1 and incubated with K562 cells that express αvβ3 (a) or mock-transfected K562 cells (b). Bound cells were quantified after gently rinsing the wells to remove non-bound cells. c) The R36E/R37E mutant did not bind to soluble integrin αvβ3. Wells of 96 well micro-titer plate were coated with IGF1 and incubated with recombinant soluble αvβ3 (5 µg/ml) in the presence of 1 mM MnCl$_2$ for 1 h at room temperature. Bound αvβ3 was determined using anti-β3 mAb and peroxidase-labeled anti-mouse IgG at OD450. Data is shown as means+/−SEM of triplicate experiments. The data indicate that the two mutants are defective in binding to integrin αvβ3. d) The R36E/R37E IGF-1 mutation did not affect the binding of IGF-1 to immobilized IGF1R. Soluble IGF1R (R&D systems) was immobilized by incubating 100 µl 1 µg/ml IGF1R in 0.1 M NaHCO$_3$ pH 9.4 overnight at 4° C. in wells of 96-well microtiter plates. Biotinylated wt IGF-1 (0.1 µg/ml) was incubated with immobilized IGF1R in the presence of increasing concentrations of non-labeled wt IGF-1, IGF-1 mutants, or irrelevant control ligand (wt FGF-1) in 100 µl PBS in wells of 96-well microtiter plates (for 3 h at room temperature). The bound biotinylated wt IGF-1 was determined using HRP-conjugated streptavidin and peroxidase substrates at 580 nm. The results suggest that the IGF-1 mutants tested and wt IGF-1 can bind to IGF1R at similar levels.

FIG. 6 The R36E/R37E IGF1 mutant was defective in inducing IGF1 intracellular signaling. Serum-starved NIH 3T3 cells (a) or C2C12 cells (b) were stimulated with 100 ng/ml IGF1 (wt or mutant) for the indicated time and the lysates were analyzed by Western blotting. (c) IGF-1 induces co-precipitation of p85 and IGF1R, but R36E/R37E did not. MCF-7 cells were serum-starved overnight and stimulated with 100 ng/ml WT or mutant IGF-1 for 10 min. Cell lysates were incubated with anti-IGF1R antibody overnight at 4 C. The immune complex was recovered by incubating with Protein A Sepharose, and analyzed by western blotting with appropriate antibodies. The results suggest that 1) total amounts of IGF1R recovered are comparable. 2) WT induced tyrosine phosphorylation of IGF1R, but R36E/R37E did not. 3) WT IGF-1 recruited p85, but R36E/R37E did not. IP, immunoprecipitation; IB, immunoblotting.

FIG. 7 The R36E/R37E IGF1 mutant was not only defective in inducing cell proliferation, but suppressed cell proliferation induced by wt IGF1. a and b) NIH 3T3 cells that express human IGF1R (NIH 3T3-IGF1R) (a) and C2C12 (b) cells were serum-starved in DMEM+0.4% FCS overnight and cultured in the presence of wt or mutant IGF1 for 24 h. The results suggest that the R36E/R37E mutant is defective in inducing cell proliferation. c and d) NIH 3T3 cells that express human IGF1R (NIH 3T3-IGF1R cells) (c) and C2C12 cells (d) were serum-starved in DMEM+0.4% FCS overnight and cultured in the presence of wt (10 ng/ml) and 10× excess R36E/R37E IGF1 (100 ng/ml) for 24 h. Controls contain wt IGF1 (10 ng/ml) only or no IGF1. The results suggest that excess R36E/R37E suppressed cell proliferation induced by wt IGF1. Cell proliferation was measured by MTS assays at OD490. Data is shown as means+/−SEM (with no IGF1 control as 100%).

Figure 8:
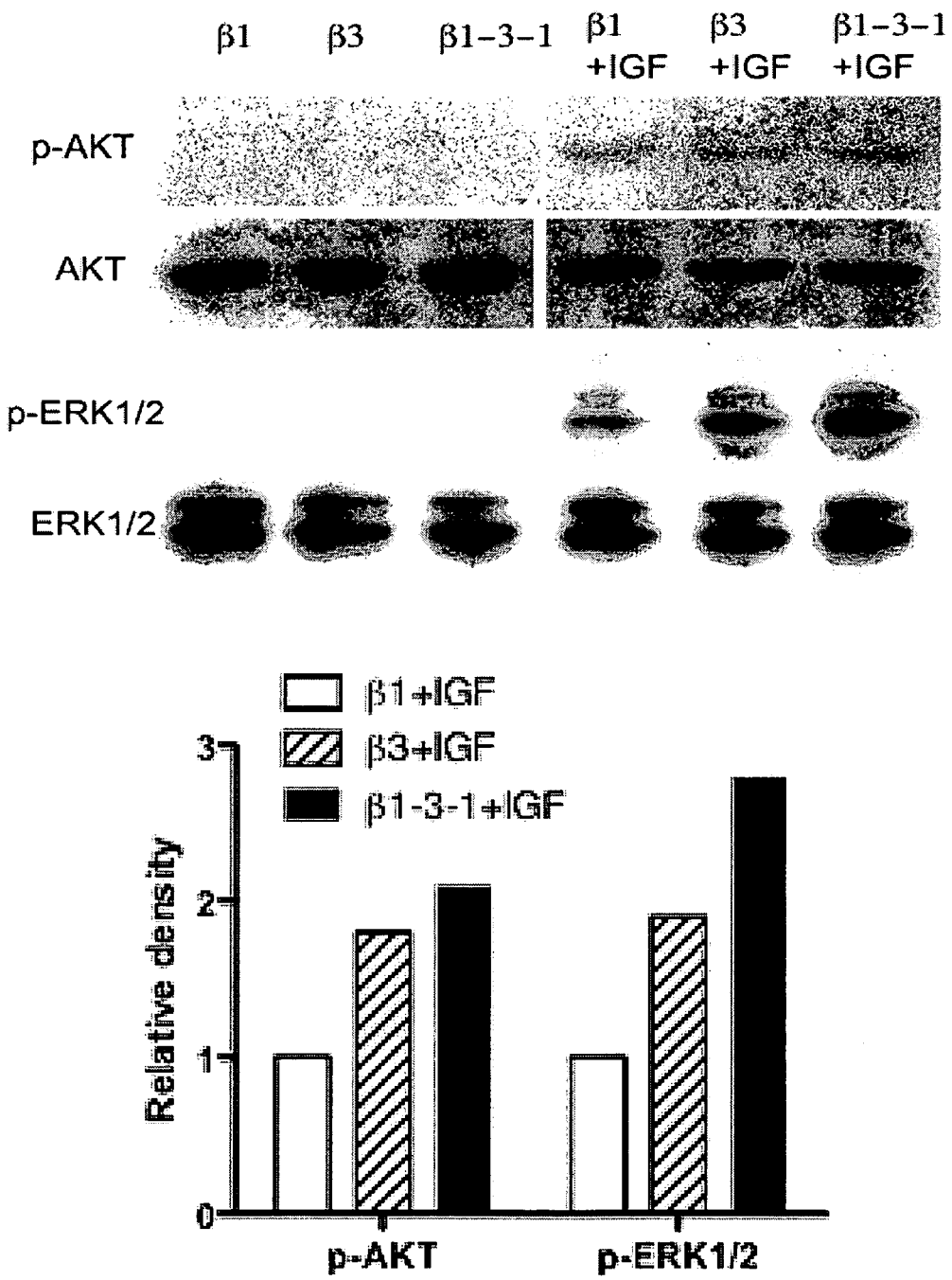

FIG. 8. The expression of β3 and β1-3-1 enhanced IGF1-induced ERK1/2 and AKT activation. Cells were serum-starved for 24 h, and then stimulated with IGF1 (100 ng/ml). We monitored activation of ERK1/2 and AKT by Western blotting of cell lysates with specific antibodies. Right panel shows relative density of p-AKT and p-ERK1/2.

Figure 9:
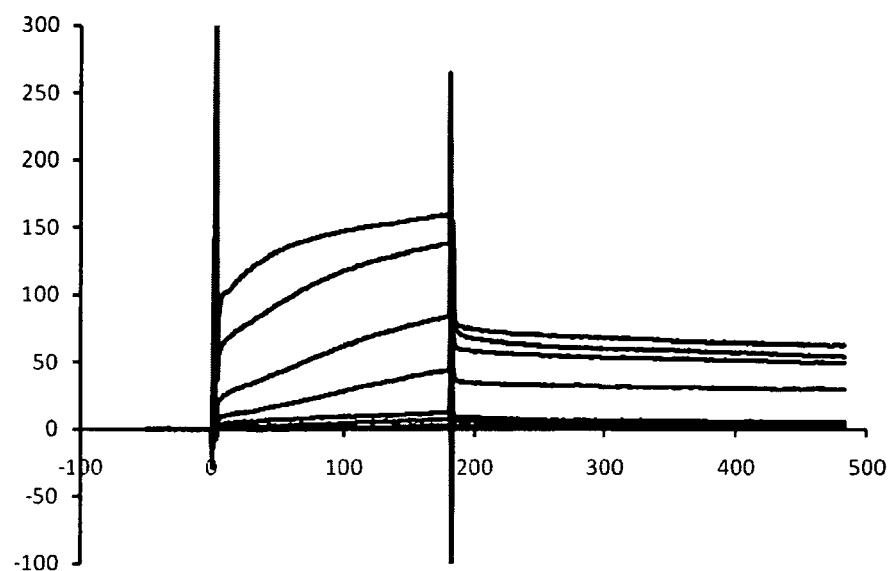

FIG. 9. Binding of wt IGF1 to αvβ3 in SPR. The y axis is "Response" and the x axis is "time" in seconds. The concentrations of wt IGF1 were 8, 4, 2, 1, 0.5, 0.25, 0.125, and 0 µM. To determine the binding affinity between IGF1s and integrin αvβ3, soluble αvβ3 was immobilized on a cm5 sensor chip. Ninety µl of the IGF1 samples in HBS (Hepes-buffered saline)-P buffer with 1 mM Mn2+ were injected and first flowed onto the reference flow cell and then continuously flowed onto the response flow cell at 50 µl/min (the association phase). After the injection, HBS-P buffer with 1 mM Mn2+ was continuously flowed over the sensor chip at 50 µl/min and allowed the bound IGF1s to dissociate from the integrin (the dissociation phase). Binding kinetics was calculated using a 1:1 binding with drifting baseline as Ka=3.33× 103 (1/Ms), Kd=1.69×10-3 (1/s), KD=5.06×10-7 (M).

Figure 10:
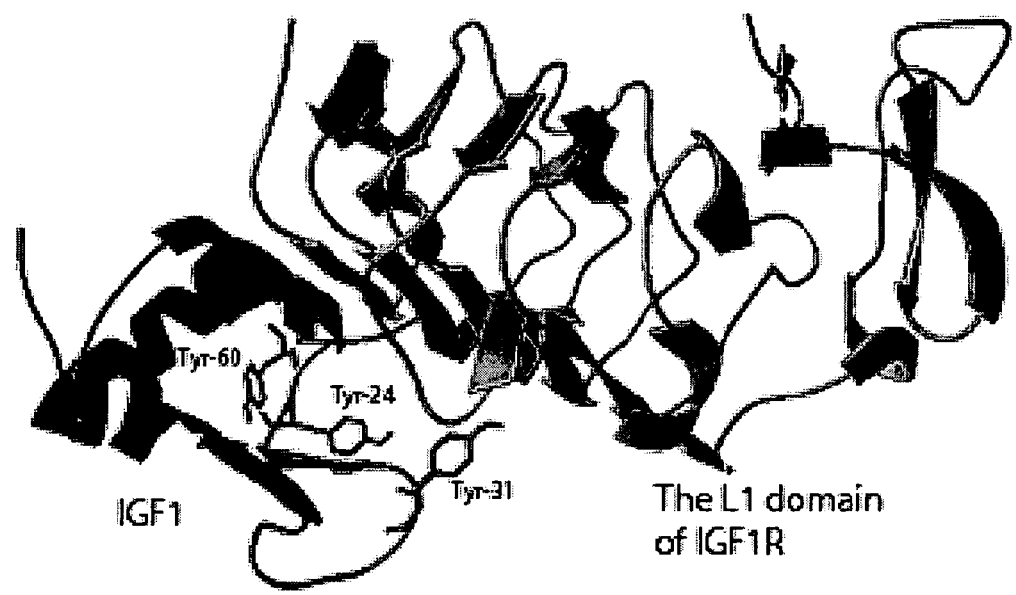

FIG. 10. A model of IGF1-IGF1R (the L1 domain) interaction. An IGF1-IGF1R L1 domain docking model was generated according to the published model (Lou et al., Natl Acad Sci USA, 2006. 103(33): p. 12429-34). Tyr residues at positions 24, 31, and 60 in the C domain of IGF1, which are important for the binding to the L1 domain of IGF1R, are located at the interface with the L1 domain.

Figure 11:
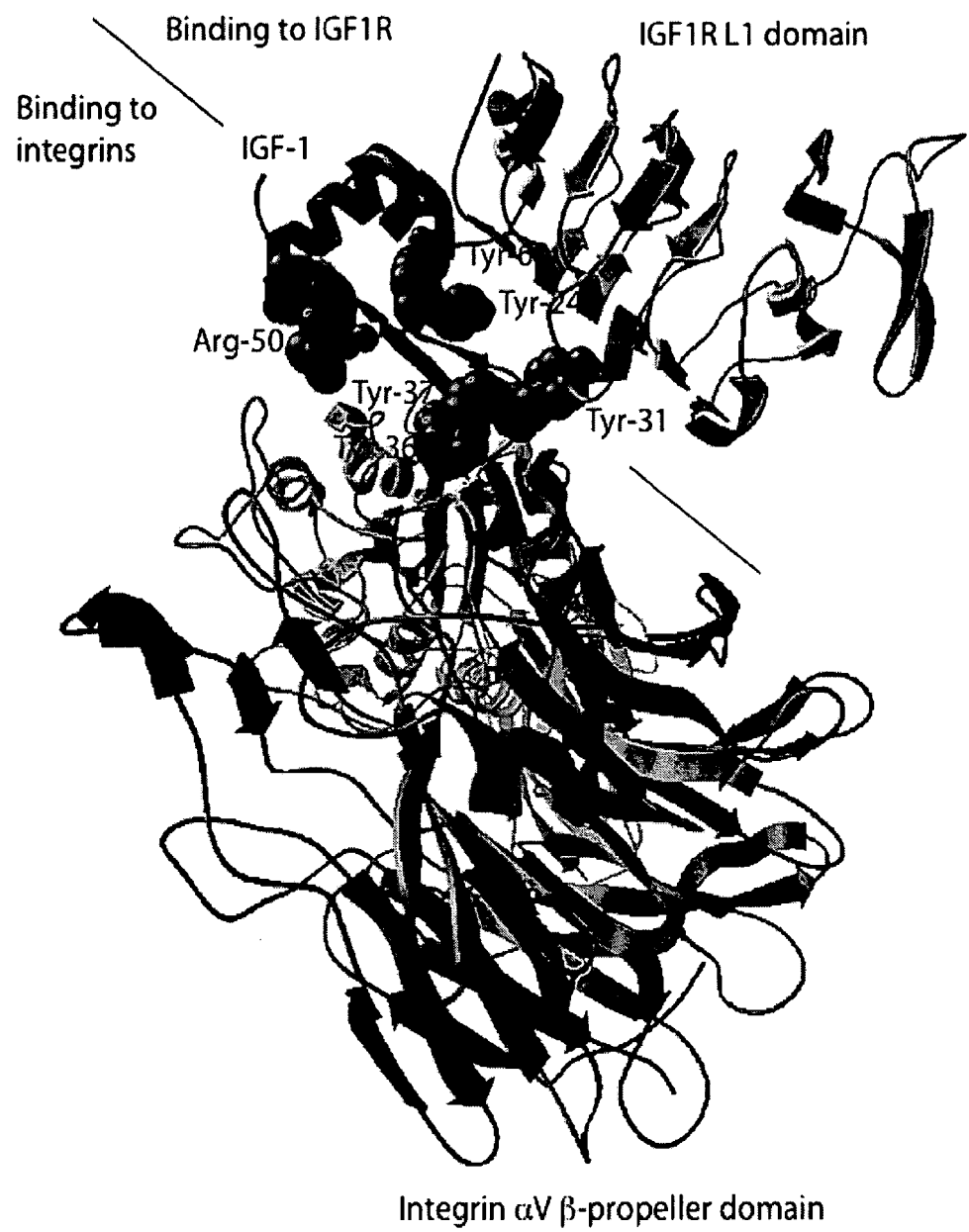

FIG. 11. A model of integrin-IGF1-IGFR interaction. An integrin-IGF1-IGF1R docking model was generated by superposing the two models (IGF1-integrin interaction and IGF1-IGF1R interaction). The model predicts that the C domain of IGF1 plays a role in both integrin and IGF binding and that the two receptors can simultaneously bind to IGF1 without steric hindrance.

FIG. 12. The R36E/R37E and R50E mutations suppressed adhesion of cells to IGF-1. Wells of 96-well microtiter plates were coated with wt and mutant IGF-1, and K562 cells that express recombinant αvβ3 or mock-transfected cells in RPMI-1640 medium were added and incubated for 1 h at 37

C. Bound cells were quantified after gentle rinsing the wells to remove unbound cells. Data is shown as means+/−SEM of triplicate experiments.

Figure 13:
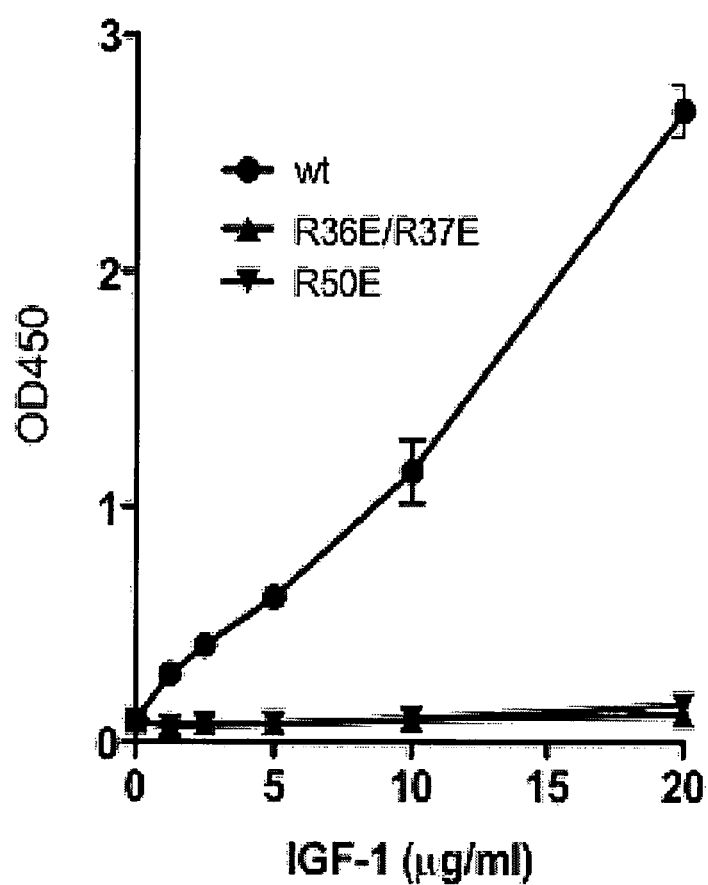

FIG. 13. The R36E/R37E and R50E mutations suppress integrin binding. Wells of 96 well microtiter plate were coated with IGF1 and incubated with recombinant soluble αvβ3 (5 μg/ml) in the presence of 1 mM MnCl2 for 1 h at room temperature. Bound αvβ3 was determined using anti-β3 mAb and peroxidase-labeled anti-mouse IgG at OD450. Data is shown as means+/−SEM of triplicate experiments. The data indicate that the two mutants are defective in binding to integrin αvβ3.

Figure 14:
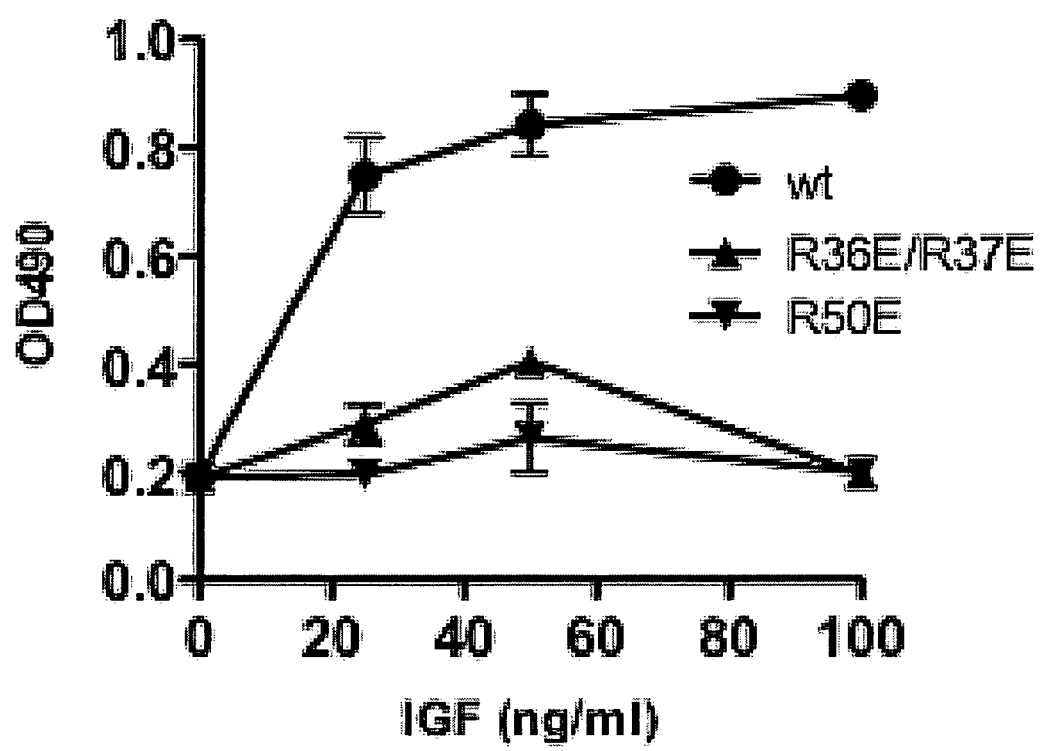

FIG. 14. The R36E/R37E and R50E IGF-1 mutants were defective in inducing proliferation of NIH 3T3 cells. NIH 3T3 cells were serum-starved in DMEM+0.4% FCS overnight and cultured in the presence of wt or mutant IGF-1 for 24 h. Cell proliferation was measured by MTS assays. Data is shown means+/−SEM (n=4). The results suggest that the R36E/R37E and R50E are defective in inducing cell proliferation (p<0.05).

Figure 15:
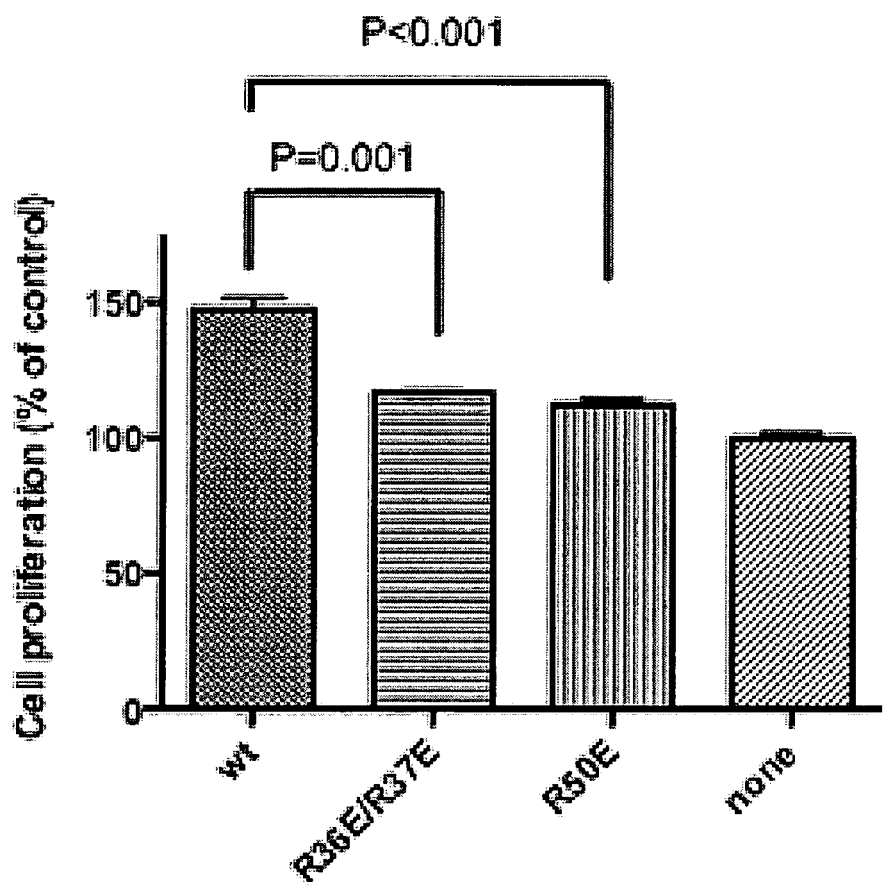

FIG. 15. Effect of the R36E/R37E and R50E mutations on IGF1 signaling in β3-CHO cells. Cells were serum-starved for 24 h, and then stimulated with IGF1 (100 ng/ml) in DMEM without FCS. The levels of cell proliferation was measured by MTS assays 24 h after stimulation. The results suggest that the IGF1 mutants were defective in inducing cell proliferation.

Figure 16:
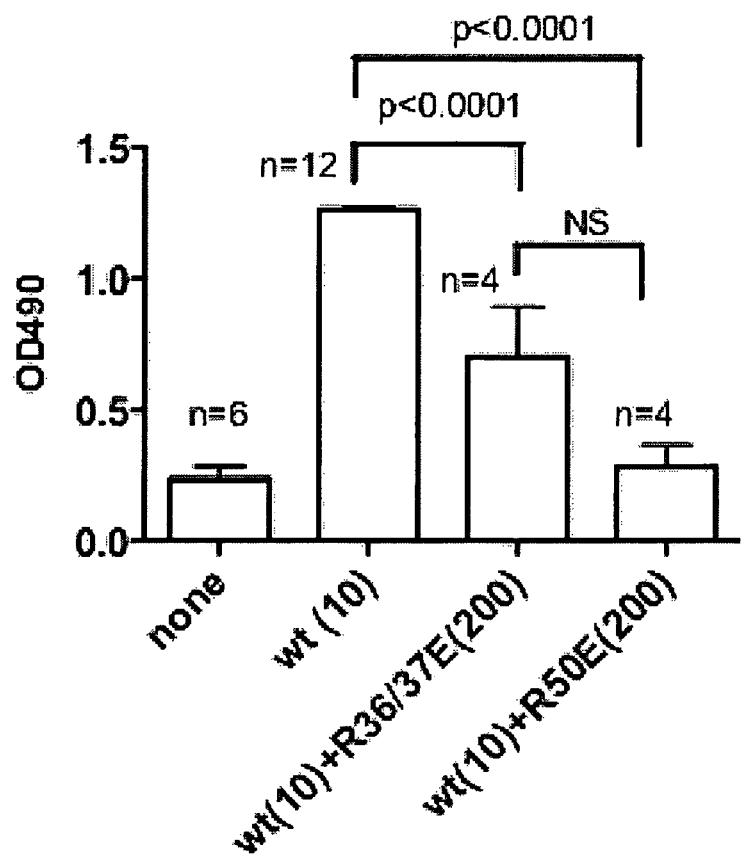

FIG. 16. Suppression of proliferation of NIH 3T3 cells induced by wt IGF-1 with integrin-binding-defective R36E/R37E and R50E mutants. NIH 3T3 cells were serum-starved in DMEM+0.4% FCS overnight and cultured in the presence of 10 ng/ml wt IGF-1 with and without 200 ng/ml mutants for 24 h. Cell proliferation was measured by MTS assays. Data is shown means+/−SEM (n=4 to 12). The results suggest that the R36E/R37E and R50E suppressed cell proliferation induced by wt IGF-1 (a dominant-negative effect by definition).

Figure 17:
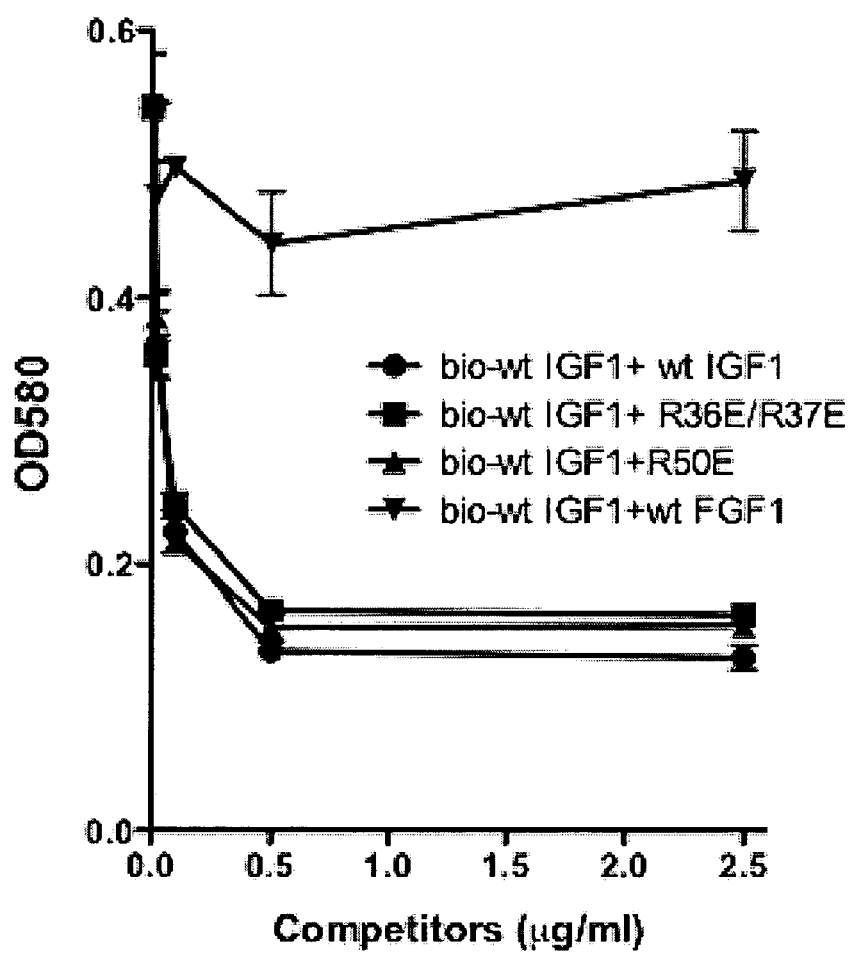

FIG. 17. The R36E/R37 and R50E IGF1 mutants suppressed the binding of biotinylated wt IGF1 to immobilized IGF1R. Soluble IGF1R (R&D systems) was immobilized by incubating 100 μl 1 μg/ml IGF1R in 0.1 M NaHCO3 pH9.4 overnight at 4 C in wells of 96-well microtiter plates. Biotinylated wt IGF1 (0.1 μg/ml) was incubated with immobilized IGF1R in the presence of increasing concentrations of non-labeled wt IGF1, IGF1 mutants, or irrelevant control ligand (wt FGF1) in 100 μl PBS in wells of 96-well microtiter plates (for 3 h at room temperature). The bound biotinylated wt IGF1 was determined using HRP-conjugated streptavidin and peroxidase substrates (SuperSignal WestPico Chemiluminescent Substrate, Pierce) at 580 nm. The results suggest that the IGF1 mutants tested and wt IGF1 can bind to IGF1R at similar levels.

Figure 18:
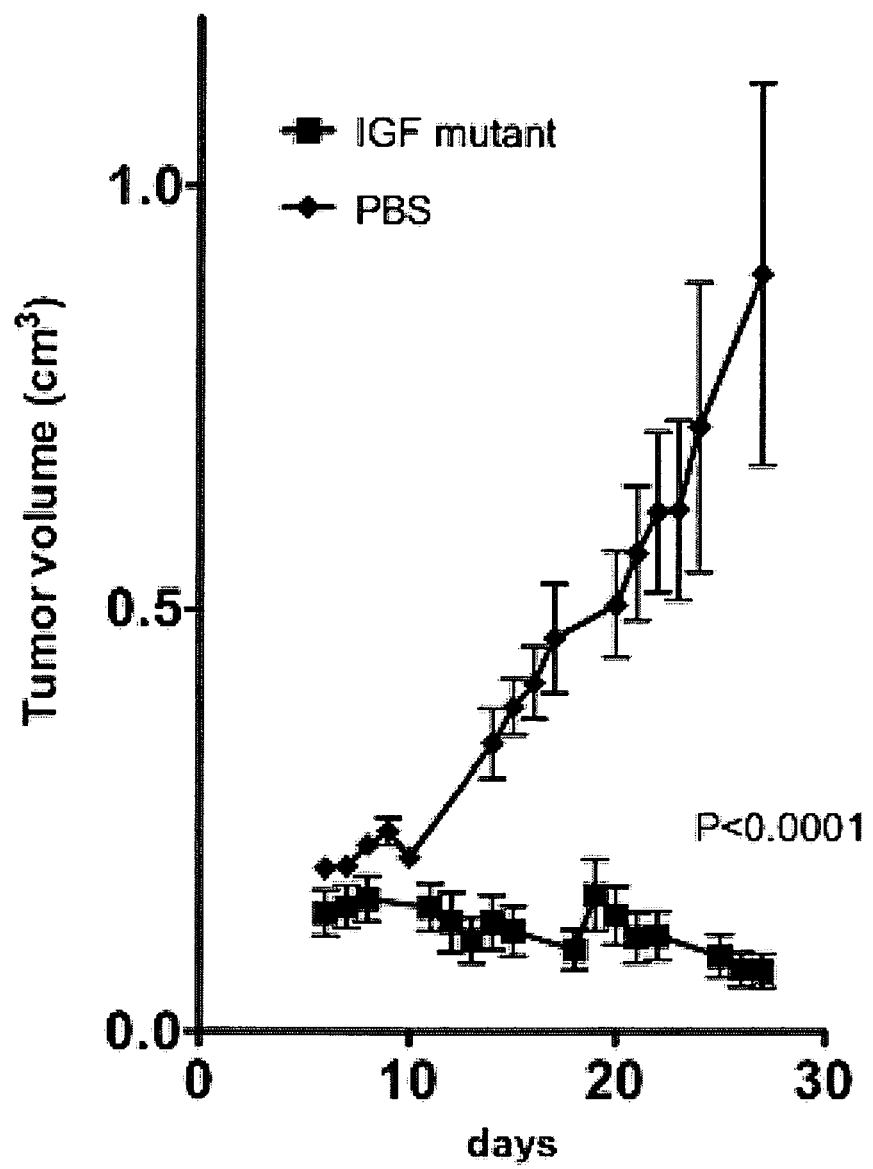

FIG. 18. Effect of daily intraperitoneal injection of R36E/R37E on tumor growth in vivo. Met-1 (a highly metastatic mouse mammary tumor) (2 mm×2 mm×2 mm) was transplanted to nude mice. R36E/R37E was then intraperitoneally injected (100 ng/mouse/day 5 days a week) starting day 3 (the mutant was injected on the day when measurement was made). The data show that R36E/R37E almost completely suppressed tumor growth at this low dose. Data is shown as means+/−SEM. P<0.0001 by 2-way ANOVA (n=6 for vehicle only control and n=8 for IGF1 R36E/R37E).

Figure 19:

FIG. 19. Whole mount mammary glands from representative FVB/N Tg (MMTV-PyV-mT) mouse. The image shows tumor development at 10 weeks of age in a nulliparous female heterozygous transgenic mouse. The vertical lines delineate zones of the #4 mammary gland with proximal (nipple) at the left. The middle line indicates the position of the intramammary lymph node consistently present in the #4 fat pad. The distal gland (far right) shows a normal branching ductal tree. The proximal gland (left) is replaced by tumor.

DEFINITIONS

The term "inhibiting" or "inhibition," as used herein, refers to any detectable negative effect on a target biological process, such as the binding between IGF1 and integrin αvβ3, or on its downstream processes including IGF1 receptor (IGF1R) phosphorylation, AKT and ERK1/2 activation, as well as cell proliferation, tumorigenicity, and metastatic potential. Typically, an inhibition is reflected in a decrease of at least 10%, 20%, 30%, 40%, or 50% in IGF1-integrin binding, or any one of the downstream parameters mentioned above, when compared to a control.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N.Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a core amino acid sequence responsible for IGF-integrin binding has at least 80% identity, preferably 85%, 90%, 91%, 92%, 93, 94%, 95%, 96%, 97%, 98%, 99%, or 100% identity, to a reference sequence, e.g., C-domain sequence of a wild-type IGF1 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0).

For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

As used herein, a "polypeptide comprising the IGF1-integrin binding region" refers to a polypeptide containing a core amino acid sequence that generally corresponds to the amino acid sequence of the C-domain of a wild-type IGF1 protein. This core amino acid sequence may contain some variations such as amino acid deletion, addition, or substitution, but should maintain a substantial level sequence homology (e.g., at least 80%, 85%, 90%, 95%, or higher sequence homology) to the C-domain sequence and is capable of binding integrin $\alpha v \beta 3$. In addition to this core sequence that is responsible for the polypeptide's ability to bind to integrin, one or more amino acid sequences of a homologous origin (e.g., additional sequence from the same protein, IGF1) or a heterologous origin (e.g., sequence from another unrelated protein) can be included in the polypeptide. Some examples of the "polypeptide comprising the IGF1-integrin binding site" include the C-domain sequence or the full length wild type IGF1. Optionally, an affinity or epitope tag (such as a GST tag) can be included in the polypeptide to facilitate purification, isolation, or immobilization of the polypeptide.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) *Nature* 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

DETAILED DESCRIPTION OF THE INVENTION

I. Introduction

It has been proposed that ligand occupancy of integrin αvβ3 with extracellular matrix ligands (e.g., vitronectin) plays a critical role in insulin-like growth factor-1 (IGF1) signaling. The present inventors found that expression of αvβ3 enhanced IGF1-induced proliferation of CHO cells in serum-free conditions (in the absence of vitronectin). It is indicated that the direct integrin binding to IGF1 plays a role in IGF1 signaling. The inventors demonstrated that αvβ3 specifically bound to IGF1, and localized the amino acid residues of IGF1 that are critical for integrin binding by docking simulation and mutagenesis. It has been found that mutations in the C-domain of IGF1 (e.g., the R36E/R37E or R50E mutation) effectively reduced integrin binding. Interestingly, these mutants were defective in inducing IGF1 receptor (IGF1R) phosphorylation, AKT and ERK1/2 activation, and in inducing cell proliferation, while retaining the ability to bind to IGF1R. Furthermore, the inventors demonstrated that the R36E/R37E mutant as well as the R50E mutant suppressed proliferation of NIH 3T3 cells induced by WT IGF1, suggesting that these mutants are dominant-negative mutants. These results indicate that the direct binding to IGF1 to integrin αvβ3 plays a role in IGF1 signaling, and integrin-IGF1 interaction is a novel target for drug discovery.

II. IGF

The insulin-like growth factors (IGFs) are polypeptides with high sequence similarity to proinsulin. IGFs are part of a complex system that cells use to communicate with their physiologic environment. This complex system (often referred to as the IGF "axis") consists of two cell-surface receptors (IGF1R and IGF2R), two ligands (IGF-1 and IGF-2), a family of six high-affinity IGF binding proteins (IGFBP 1-6), as well as associated IGFBP degrading enzymes, referred to collectively as proteases.

Wild type, or mature wild type, human insulin-like growth factor 1 (IGF1) is a 70-amino acid protein (SEQ ID NO:1) that has many growth-promoting and metabolic activities. IGF-1 is a member of the insulin superfamily, which includes insulin, IGF-2, relaxin, bombyxin, and the molluscan insect peptides. Precursor insulin-like growth factor 1 is a 153-amino acid protein (SEQ ID NO:7; Swiss-prot number P01343.1). mRNA of the precursor IGF1 is shown in SEQ ID NO:8 (GeneBank number M27544.1).

The first 29 residues of IGF-1 are homologous to the B-chain of insulin (B region; residues 1-29 of SEQ ID NO:1), followed by 12 residues that are analogous to the C-peptide of proinsulin ("C region"; or "C-domain"; residues 30-41 of SEQ ID NO:1), and a 21-residue region that is homologous to the A-chain of insulin (A region; residues 42-62 of SEQ ID NO:1). The carboxyl-terminal octapeptide (D region; residues 63-70 of SEQ ID NO:1) has no counterpart in the insulins. The IGFs are the only members of the superfamily in which the C region is not removed proteolytically after translation.

The IGFs are able to bind to more than one receptor; IGF-1 binds with highest affinity to the IGF-1 receptor, a receptor structurally homologous to the insulin receptor with which it crossreacts with lower affinity. The growth-promoting effects of insulin and the metabolic activity of IGF-1 are thought to arise from crossbinding to each other's receptors. Ligand-receptor specificity in the insulin and IGF-1 systems is determined by the sequence differences between the two ligands and the common binding sites of the two receptors, respectively.

The "C region" or "C-domain" of IGF1 is critical for integrin binding. In addition, part of the "A region," e.g., R50, is also involved in integrin binding. Residues from A, B and C regions, e.g., Y24, Y31, and Y60, are found to be involved in IGF receptor binding.

III. Dominant-Negative Mutants

As used herein, "dominant negative mutant" refers to variant forms of a protein that inhibit the activity of the endogenous, wild type form of the protein (i.e., IGF or IGF1). In the context of the present invention, a dominant negative mutant of IGF or IGF1 polypeptide is an IGF or IGF1 polypeptide that has been modified (e.g., by mutation of one or more amino acid residues, by posttranscriptional modification, by posttranslational modification) such that the dominant negative IGF or IGF1 inhibits the activity of the endogenous IGF or IGF1. For example, in the context of the present invention, the dominant negative IGF or IGF1 inhibits IGF signaling. In some embodiments, the dominant negative IGF or IGF1 inhibits IGF-integrin binding. In some embodiments, the dominant negative IGF or IGF1 inhibits IGF-IGF receptor binding.

The dominant negative IGF or IGF1 can be a polypeptide having an amino acid sequence substantially similar (i.e., at least about 75%, about 80%, about 85%, about 90%, about 95% similar) to the wild type IGF or IGF1. The dominant negative IGF or IGF1 can also be a polypeptide comprising a fragment of the wild type IGF or IGF1, e.g., the C-domain of the wild-type IGF1 protein. For example, the dominant negative IGF or IGF1 comprises the integrin binding region of the wild type IGF or IGF1, or the IGF-IGF receptor binding region of the wild-type IGF1 protein. A dominant negative IGF polypeptide can bind only one of integrin and IGF receptor, but not both.

The dominant negative IGF or IGF1 can be a truncated form of the wild type IGF or IGF1. For example, the dominant negative IGF1 is a truncated IGF1 lacking one or more A, B, C, and D regions, e.g., a truncated IGF1 lacking C region.

The dominant negative IGF or IGF1 can have an amino acid sequence of wild type IGF or IGF1 or fragments thereof except Arg residues at positions 36, 37, or 50 in the wild type IGF1 (positions 36, 37, and 50 are defined by the numbering set forth in SEQ ID NO:1) is deleted or substituted with amino acid that results in inhibition of IGF-signaling. In one example, the dominant negative IGF or IGF1 is an R36E/R37E mutant. In another example, the dominant negative IGF or IGF1 is an R50E mutant. The R36E, R37E, R50E, and R36E/R37E mutants, as defined herein, can be a full-length IGF1 or fragments thereof.

The dominant negative IGF or IGF1 can have an amino acid sequence of wild type IGF or IGF1 or fragments thereof except Tyr residues at positions 24, 31, or 60 in the wild type IGF1 (positions 24, 31, and 60 are defined by the numbering set forth in SEQ ID NO:1) is deleted or substituted with amino acid that results in inhibition of IGF-signaling.

The dominant negative mutants of the present invention can be used for inhibiting IGF signaling in a cell, i.e., by contacting the cell with an effective amount of a dominant negative mutant of the present invention. The dominant negative IGF or IGF1 can be modified, e.g., to extend in vivo half-life, by PEGylation or incorporation of long-chain polyethylene glycol polymers (PEG). Introduction of PEG or long chain polymers of PEG increases the effective molecular weight of the present polypeptides, for example, to prevent rapid filtration into the urine. In some embodiments, a Lysine residue in the dominant negative IGF or IGF1 is conjugated to PEG directly or through a linker. Such linker can be, for example, a Glu residue or an acyl residue containing a thiol functional group for linkage to the appropriately modified PEG chain. An alternative method for introducing a PEG chain is to first introduce a Cys residue at the C-terminus or at solvent exposed residues such as replacements for Arg or Lys residues. This Cys residue is then site-specifically attached to a PEG chain containing, for example, a maleimide function. Methods for incorporating PEG or long chain polymers of PEG are well known in the art (described, for example, in Veronese, F. M. et al., *Drug Disc. Today* 10: 1451-8 (2005); Greenwald, R. B. et al., *Adv. Drug Deliv. Rev.* 55: 217-50 (2003); Roberts, M. J. et al., *Adv. Drug Deliv. Rev.*, 54: 459-76 (2002)), the contents of which is incorporated herein by reference. Other methods of polymer conjugations known in the art can also be used in the present invention. In some embodiments, poly(2-methacryloyloxyethyl phosphorylcholine) (PMPC) is introduced as a polymer conjugate with the dominant negative IGF or IGF1 of the invention (see, e.g., WO2008/098930; Lewis et al., *Bioconjug Chem.*, 19: 2144-55 (2008)). In some embodiments, a phosphorylcholine-containing polymer conjugate with the dominant negative IGF or IGF1 can be used in the present invention. A person of skill would readily recognize that other biocompatible polymer conjugates can be utilized.

IV. Production of IGF-Related Polypeptides

A. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of an IGF1 gene, a polynucleotide encoding a polypeptide comprising the integrin-binding sequence of IGF1, and synthetic oligonucleotides can be verified after cloning or subcloning using, e.g., the chain termination method for sequencing double-stranded templates of Wallace et al., *Gene* 16: 21-26 (1981).

B. Coding Sequence for a IGF1-Related Polypeptide

Polynucleotide sequences encoding a wild-type IGF1 protein, especially a wild-type human IGF1 protein, have been determined and may be obtained from a commercial supplier.

The rapid progress in the studies of human genome has made possible a cloning approach where a human DNA sequence database can be searched for any gene segment that has a certain percentage of sequence homology to a known nucleotide sequence, such as one encoding a previously identified human IGF. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a human IGF can be isolated from a human cDNA or genomic DNA library using standard cloning techniques such as polymerase chain reaction (PCR), where homology-based primers can often be derived from a known nucleic acid sequence encoding an IGF. Most commonly used techniques for this purpose are described in standard texts, e.g., Sambrook and Russell, supra.

cDNA libraries suitable for obtaining a coding sequence for a human IGF may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene*, 25: 263-269 (1983); Ausubel et al., supra). Upon obtaining an amplified segment of nucleotide sequence by PCR, the segment can be further used as a probe to isolate the full length polynucleotide sequence encoding the IGF from the cDNA library. A general description of appropriate procedures can be found in Sambrook and Russell, supra.

A similar procedure can be followed to obtain a full-length sequence encoding a human IGF from a human genomic library. Human genomic libraries are commercially available or can be constructed according to various art-recognized methods. In general, to construct a genomic library, the DNA is first extracted from a tissue where an IGF is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science*, 196: 180-182 (1977). Colony hybridization is carried out as described by Grunstein et al., *Proc. Natl. Acad. Sci. USA*, 72: 3961-3965 (1975).

Based on sequence homology, degenerate oligonucleotides can be designed as primer sets and PCR can be performed under suitable conditions (see, e.g., White et al., *PCR Protocols: Current Methods and Applications*, 1993; Griffin and Griffin, *PCR Technology*, CRC Press Inc. 1994) to amplify a segment of nucleotide sequence from a cDNA or genomic library. Using the amplified segment as a probe, the full-length nucleic acid encoding a IGF is obtained.

Upon acquiring a nucleic acid sequence encoding an IGF, the coding sequence can be further modified by a number of well known techniques such as restriction endonuclease digestion, PCR, and PCR-related methods to generate coding sequences for IGF-related polypeptides, including IGF mutants (especially the dominant-negative type) and polypeptides comprising an integrin-binding sequence derived from an IGF. The polynucleotide sequence encoding a desired IGF-related polypeptide can then be subcloned into a vector, for instance, an expression vector, so that a recombinant polypeptide can be produced from the resulting construct. Further modifications to the coding sequence, e.g., nucleotide substitutions, may be subsequently made to alter the characteristics of the polypeptide.

A variety of mutation-generating protocols are established and described in the art, and can be readily used to modify a polynucleotide sequence encoding a IGF-related polypeptide. See, e.g., Zhang et al., *Proc. Natl. Acad. Sci. USA*, 94: 4504-4509 (1997); and Stemmer, *Nature*, 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other possible methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

C. Modification of Nucleic Acids for Preferred Codon Usage in a Host Organism

The polynucleotide sequence encoding a IGF-related polypeptide, such as a dominant negative IGF polypeptide, can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the IGF-related polypeptides.

D. Chemical Synthesis of IGF-Related Polypeptides

The amino acid sequence of integrin-bind site derived from human IGF1, such as the C-domain sequence of IGF1, is provided. A polypeptide comprising this IGF1-integrin binding sequence thus can also be chemically synthesized using conventional peptide synthesis or other protocols well known in the art.

Polypeptides may be synthesized by solid-phase peptide synthesis methods using procedures similar to those described by Merrifield et al., *J. Am. Chem. Soc.*, 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach*, IRL Press (1989), and Bodanszky, *Peptide Chemistry, A Practical Textbook*, 2nd Ed., Springer-Verlag (1993)).

V. Expression and Purification of IGF-Related Polypeptides

Following verification of the coding sequence, a IGF-related polypeptide of the present invention can be produced using routine techniques in the field of recombinant genetics, relying on the polynucleotide sequences encoding the polypeptide disclosed herein.

A. Expression Systems

To obtain high level expression of a nucleic acid encoding a IGF-related polypeptide of the present invention, one typically subclones a polynucleotide encoding the polypeptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the IGF-related polypeptide in host cells. A typical expression cassette thus contains a promoter operably linked to the nucleic acid sequence encoding the IGF-related polypeptide and signals required for efficient polyadenylation of the transcript, ribosome binding sites, and translation termination. The nucleic acid sequence encoding the IGF-related polypeptide is typically linked to a cleavable signal peptide sequence to promote secretion of the polypeptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the NRG-related polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., a IGF-related polypeptide of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

A person skilled in the art will recognize that various conservative substitutions can be made to any wild-type or mutant IGF or a polypeptide comprising an integrin-binding sequence of IGF, to produce a modified polypeptide that, while still retaining the ability to bind integrin, does not trigger IGF downstream signaling. Moreover, modifications of a polynucleotide coding sequence may also be made to accommodate preferred codon usage in a particular expression host without altering the resulting amino acid sequence.

B. Transfection Methods

Standard transfection methods are used to produce bacterial, mammalian, yeast, insect, or plant cell lines that express large quantities of a NRG-related polypeptide, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the IGF-related polypeptide.

C. Purification of Recombinantly Produced IGF-Related Polypeptides

Once the expression of a recombinant IGF-related polypeptide in transfected host cells is confirmed, e.g., via an immunoassay such as Western blotting assay, the host cells are then cultured in an appropriate scale for the purpose of purifying the recombinant polypeptide.

1. Purification of Recombinantly Produced Polypeptides from Bacteria

When the IGF-related polypeptides of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Additional methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., an IGF-related polypeptide, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide of the present invention, e.g., an IGF mutant or a polypeptide comprising an IGF-integrin binding sequence, is expressed in host cells in a soluble form, its purification can follow the standard protein purification procedure described below. This standard purification procedure is also suitable for purifying IGF-related polypeptides obtained from chemical synthesis.

i. Solubility Fractionation

Often as an initial step, and if the protein mixture is complex, an initial salt fractionation can separate many of the unwanted host cell proteins (or proteins derived from the cell culture media) from the recombinant protein of interest, e.g., an IGF-related polypeptide of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., an IGF-related polypeptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The proteins of interest (such as an IGF-related polypeptide of the present invention) can also be separated from other proteins on the basis of their size, net surface charge, hydrophobicity, or affinity for ligands. In addition, antibodies raised against a segment of IGF such as the integrin-binding site can be conjugated to column matrices and the IGF-related polypeptide immunopurified. All of these methods are well known in the art.

It will be apparent to one of skill that chromatographic techniques can be performed at any scale and using equipment from many different manufacturers (e.g., Pharmacia Biotech).

VI. Identification of Inhibitors for IGF-Integrin Binding

A. IGF-Integrin Binding Assays

An in vitro assay can be used to detect IGF-integrin binding and to identify compounds that are capable of inhibiting IGF-integrin binding. In general, such an assay can be performed in the presence of an IGF, such as human IGF1, and an integrin, such as αvβ3, that are known to bind each other, under conditions permitting such binding. For convenience, one of the binding partners may be immobilized onto a solid support and/or labeled with a detectable moiety. A third molecule, such as an antibody (which may include a detectable label) to one of the binding partners, can also be used to facilitate detection.

In some cases, the binding assays can be performed in a cell-free environment; whereas in other cases, the binding assays can be performed on cell surface, frequently using cells recombinantly or endogenously expressing an appropriate integrin molecule. More details and some examples of such binding assays can be found in the Examples section of this application.

To screen for compounds capable of inhibiting IGF-integrin binding, the above-described assays are performed both in the presence and absence of a test compound, the level of IGF-integrin binding is then compared. If IGF-integrin binding is suppressed at the presence of the test compound at a level of at least 10%, more preferably at least 20%, 30%, 40%, or 50%, or even higher, the test compound is then deemed an inhibitor of IGF-integrin binding and may be subject to further testing to confirm its ability to inhibit IGF signaling.

The binding assay is also useful for confirming that a polypeptide comprising an integrin-binding sequence derived from an IGF can indeed specifically bind integrin. For instance, a polypeptide comprising the C-domain of an IGF1 protein but not the full length IGF1 sequence may be recombinantly expressed, purified, and placed in a binding assay with integrin αvβ3, substituting a full length wild type IGF1 protein, which is used in a control assay to provide a comparison basis. If deemed to have sufficient integrin-binding ability, a polypeptide comprising an IGF1-integrin binding sequence can then be used, in place of a wild-type full length IGF1 protein, in a binding assay for identifying inhibitors of IGF1-integrin binding. Similarly, a polypeptide comprising a core sequence with a high level of homology (e.g., 90%, 95% or higher) to C-domain sequence of a wild-type IGF1 protein can be tested and, if appropriate, can be used, in place of a wild-type full length IGF1 protein, in a binding assay for identifying inhibitors of IGF1-integrin binding.

Inhibitors of IGF1-integrin binding can have diverse chemical and structural features. For instance, an inhibitor can be a non-functional IGF1 mutant that retaining integrin-binding ability, an antibody to either IGF1 or integrin that interferes with IGF1-integrin binding, or any small molecule or macromolecule that simply hinders the interaction between IGF1 and integrin. Essentially any chemical compound can be tested as a potential inhibitor of IGF1-integrin binding. Most preferred are generally compounds that can be dissolved in aqueous or organic (especially DMSO-based) solutions. Inhibitors can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science,* 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

B. IGF1 Signaling Assays

The inhibitors of IGF-integrin binding are useful for their ability to inhibit IGF1 signaling, especially as anti-cancer therapeutics for cancer patients overexpressing one or more integrin molecules. Assays for confirming such inhibitory effect of an inhibitor can be performed in vitro or in vivo. An in vitro assay typically involves exposure of cultured cells to an inhibitor and monitoring of subsequent biological and biochemical changes in the cells. For example, following exposure to 0.1-20 µg/ml an inhibitor for 0.5-48 hours, suitable cells (such as those expressing integrin αvβ3) are examined for their proliferation/survival status using methods such as direct cell number counting, BrdU or $H^3$-thymidine incorporation, tetrazolium salt 3,[4,5-dimethylthiazol-2-yl]-2,5-diphenyltetrazolium bromide (MTT) cell proliferation assay, 3-(4,5-dimethylthiazol-2-yl)-5-(3-carboxymethoxyphenyl)-2-(4-sulfophenyl)-2H-tetrazolium (MTS) cell proliferation assay, chicken embryo allantoic membrane (CAM) assay, TUNNEL assay, annexin V binding assay, etc. Further downstream changes due to IFG1 signaling, e.g., phosphorylation of IFG1R, AKT or ERK1/2 activation, can also be monitored to provide an indication of suppressed ErbB signaling. In addition, tumorigenicity of cancer cells is useful parameters for monitoring and can be tested by methods such as colony formation assays or soft agar assays. Detailed description of some exemplary assays can be found in the Examples section of this disclosure. An inhibitory effect is detected when a decrease in IFG signaling, as indicated by any one aforementioned parameter, of at least 10%, 20%, 30%, 40%, 50%, 60%, 70%, 80%, 90% or more is observed.

The effects of a IGF1-integrin binding inhibitor of the present invention can also be demonstrated in in vivo assays. For example, an inhibitor of IGF1-integrin can be injected into animals that have a compromised immune system (e.g., nude mice, SCID mice, or NOD/SCID mice) and therefore permit xenograft tumors. Injection methods can be intravenous, intraperitoneal, or intratumoral in nature. Tumors development is subsequently monitored by various means, such as measuring tumor volume and scoring secondary lesions due to metastases, in comparison with a control group of animals with similar tumors but not given the inhibitors. The Examples section of this disclosure provides detailed description of some exemplary in vivo assays. An inhibitory effect is detected when a negative effect on tumor growth or metastasis is established in the test group. Preferably, the negative effect is at least a 10% decrease; more preferably, the decrease is at least 20%, 30%, 40%, 50%, 60%, 70%, 80%, or 90%.

VII. Pharmaceutical Compositions and Administration

The present invention also provides pharmaceutical compositions or physiological compostions comprising an effective amount of a compound that inhibits IGF-integrin binding, such as a dominant negative IGF1 mutant R36E/R37E or R50E, or its encoding nucleic acid, inhibiting IGF signaling in both prophylactic and therapeutic applications. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal. The preferred routes of administering the pharmaceutical compositions are local delivery to an organ or tissue suffering from a condition exacerbated by IGF overexpression (e.g., intratumor injection to a tumor) at daily doses of about 0.01-5000 mg, preferably 5-500 mg, of an IGF-integrin binding inhibitor for a 70 kg adult human per day. The appropriate dose may be administered in a single daily dose or as divided doses presented at appropriate intervals, for example as two, three, four, or more subdoses per day.

For preparing pharmaceutical compositions containing an IGF-integrin inhibitor, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an IGF1 dominant negative mutant polypeptide. In tablets, the active ingredient (an inhibitor of IGF1-integrin binding) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of an inhibitor of IGF-integrin binding. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of a IGF-integrin binding inhibitor with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a dominant-negative IGF1 mutant polypeptide) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an IGF-integrin binding inhibitor) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing IGF-integrin binding inhibitors can be administered for prophylactic and/or therapeutic treatments. In therapeutic applications, compositions are administered to a patient already suffering from a condition that may be exacerbated by the overexpression of IGF or integrin family members in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the inhibitor per day for a 70 kg patient, with dosages of from about 5 mg to about 500 mg of the inhibitor per day for a 70 kg patient being more commonly used.

In prophylactic applications, pharmaceutical compositions containing IGF-integrin binding inhibitors are administered to a patient susceptible to or otherwise at risk of developing a disease or condition in which overexpression of IGF or integrin is undesirable, in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,000 mg of the inhibitor for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of an IGF-integrin binding sufficient to effectively inhibit IGF signaling in the patient, either therapeutically or prophylatically.

VIII. Therapeutic Applications Using Nucleic Acids

A variety of diseases can be treated by therapeutic approaches that involve introducing a nucleic acid encoding a polypeptide inhibitor of integrin-IGF binding into a cell such that the coding sequence is transcribed and the polypeptide inhibitor is produced in the cell. Diseases amenable to treatment by this approach include a broad spectrum of solid tumors, the survival and growth of which rely on to some extent the continued signaling of IGF or integrin family members. For discussions on the application of gene therapy towards the treatment of genetic as well as acquired diseases, see, Miller *Nature* 357:455-460 (1992); and Mulligan *Science* 260:926-932 (1993).

A. Vectors for Gene Delivery

For delivery to a cell or organism, a polynucleotide encoding a polypeptide that inhibits IGF-integrin binding (such as the dominant-negative mutant R36E/R37E or R50E) can be incorporated into a vector. Examples of vectors used for such purposes include expression plasmids capable of directing the expression of the nucleic acids in the target cell. In other instances, the vector is a viral vector system wherein the polynucleotide is incorporated into a viral genome that is capable of transfecting the target cell. In a preferred embodiment, the polynucleotide encoding a polypeptide inhibitor can be operably linked to expression and control sequences that can direct expression of the polypeptide in the desired target host cells. Thus, one can achieve expression of the polypeptide inhibitor under appropriate conditions in the target cell.

B. Gene Delivery Systems

Viral vector systems useful in the expression of a polypeptide inhibitor of IGF-integrin binding include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the genes of interest (e.g., one encoding for a polypeptide inhibitor of the present invention) are inserted into such vectors to allow packaging of the gene construct, typically with accompanying viral DNA, followed by infection of a sensitive host cell and expression of the gene of interest.

As used herein, "gene delivery system" refers to any means for the delivery of a nucleic acid of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors may also be useful for introducing the coding sequence of a polypeptide inhibitor of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.,* 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide of the invention and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA,* 81:6349-6353 (1984); Danos and Mulligan *Proceedings of the National Academy of Sciences, USA,* 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

C. Pharmaceutical Formulations

When used for pharmaceutical purposes, the nucleic acid encoding an IGF-integrin binding inhibitor polypeptide is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in *Remington's Pharmaceutical Sciences*, Mack Publishing Company, Philadelphia, Pa., 17th ed. (1985).

D. Administration of Formulations

The formulations containing a nucleic acid encoding a polypeptide inhibitor of the binding between IGF and integrin can be delivered to any tissue or organ using any delivery method known to the ordinarily skilled artisan. In some embodiments of the invention, the nucleic acids encoding the inhibitor polypeptides are formulated for intravenous, intraperitoneal, or intratumor injection.

The formulations containing the nucleic acid of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, ultrasound, electroporation, or biolistics. In further embodiments, the nucleic acids are taken up directly by the tissue of interest.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6): 2414-9 (1996); Koc et al., *Seminars in Oncology* 23(1):46-65 (1996); Raper et al., *Annals of Surgery* 223(2):116-26 (1996); Dalesandro et al., *J. Thorac. Cardi. Surg.,* 11(2):416-22 (1996); and Makarov et al., *Proc. Natl. Acad. Sci. USA* 93(1): 402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of the vector to be administered, the physician should evaluate the particular nucleic acid used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present invention, doses ranging from about 10 ng-1 g, 100 ng-100 mg, 1 µg-10 mg, or 30-300 µg DNA per patient are typical. Doses generally range between about 0.01 and about 50 mg per kilogram of body weight, preferably between about 0.1 and about 5 mg/kg of body weight or about $10^8$-$10^{10}$ or $10^{12}$ particles per injection. In general, the dose equivalent of a naked nucleic acid from a vector is from about 1 µg-100 µg for a typical 70 kg patient, and doses of vectors which include a retroviral particle are calculated to yield an equivalent amount of nucleic acid encoding a polypeptide that inhibits the binding between integrin and IGF (e.g., human IGF1).

IX. Kits

The invention also provides kits for inhibiting IGF1 signaling according to the method of the present invention. The kits typically include a container that contains a pharmaceutical composition having an effective amount of an inhibitor of IGF-integrin binding (such as a dominant-negative mutant R36E/R37E or R50E or a polynucleotide sequence encoding the polypeptide) as well as informational material containing instructions on how to dispense the pharmaceutical composition, including description of the type of patients who may be treated (e.g., cancer patients with IGF1 or integrin overexpression), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Example 1

Experimental Procedures

Materials

7E3, and AIIB2 hybridomas were obtained from ATCC. CHO cells that express human β3, β1, and the β1-3-1 mutant have been described (Takagi et al., J Biol Chem 272(32): 19794-800, 1997). The human IGF1R expression construct (Slaaby et al., J Biol Chem 281(36): 25869-74, 2006) was kindly provided by Rita Slaaby (Novo Nordisk A/S, Måløv, Denmark).

Methods

Synthesis of IGF1

A cDNA fragment encoding IGF1 was amplified by PCR with synthetic oligonucleotides 5'-ccgacgcatCCATGGctg-gaccggagacgctctgc-3' (SEQ ID NO: 2) and 5'-gtggtgctc-gagagctgacttggcaggcttgag-3' (SEQ ID NO: 3) with human placenta cDNA library as a template. After Nco I/Xho I digestion, the cDNA fragment was subcloned into the Nco I/Xho I site of PET28a vector. The expression construct encodes wild type IGF-1 with a 6His-tag (SEQ ID NO:9) at the C-terminus, MGPETLCGAELVDALQFVCGDRGFY-FNKPTGYGSSSRRAPQTGIVDECCFRSCDLRRLE MYCAPLKPAKSALEHHHHHH (SEQ ID NO: 4). The expression construct encodes IGF-1 R36E/R37E mutant with a 6His-tag (SEQ ID NO:9) at the C-terminus, MGPETL-CGAELVDALQFVCGDRGFYFNKPT-GYGSSSEEAPQTGIVDECCFRSCDLRRLE MYCAPLK-PAKSALEHHHHHH (SEQ ID NO: 5). The expression construct encodes IGF-1 R50E with a 6His-tag (SEQ ID NO:9) at the C-terminus, MGPETL-CGAELVDALQFVCGDRGFYFNKPT-GYGSSSRRAPQTGIVDECCFESCDLRRLE MYCAPLK-PAKSALEHHHHHH (SEQ ID NO: 6). Protein was expressed in E. coli BL21 as insoluble proteins and purified using Ni-NTA affinity chromatography under denaturing conditions. To remove endotoxin, the Ni-NTA resin was washed with 1% Triton X-114 before eluting the bound protein. Purified proteins were refolded in vitro following the protocols ("Isolation of proteins from inclusion bodies" in www.its.caltech.edu/~bjorker/protocols/). Briefly, purified proteins in 8 M urea were diluted into refolding buffer (100 mM Tris-HCl, pH 8.0, 400 mM L-Arg, 2 mM EDTA, 0.5 mM oxidized glutathione, 5 mM reduced glutathione, and protease inhibitors) and kept for 8 h at 4° C., and then concentrated by ultrafiltration.

Cell Proliferation

Cell proliferation was assessed based on the ability of the cells to convert MTS into formazan, using the Aqueous Cell Proliferation Assay Kit (Promega, Madison, Wis.). Cells were plated in 96-well plates ($1 \times 10^4$ cells/well), and then incubated with DMEM containing 10% FBS at 37° C. in 5% $CO_2$ atmosphere. Twenty μl of MTS reagent was added to each well at the indicated time period. Relative cell number was measured based on increased absorbance at 490 nm.

Western Blot Analysis

Cells were cultured to nearly confluent in DMEM supplemented with 10% FBS, and then maintained in DMEM without fetal bovine serum (FBS) for 24 h. The starved cells were treated with WT or mutant IGF1 (100 ng/ml) in DMEM without FBS for the time indicated. Cells were then solubilized in lysis buffer (1% Nonidet P-40, 0.5% sodium deoxycholate, 0.1% SDS in phosphate-buffered saline, pH 7.4) containing 1 mM PMSF, 10 μg/ml aprotinin, and 10 μg/ml leupeptin at 4° C. for 30 min. After Centrifugation at 12,000×g for 15 min, the supernatant were removed and the protein concentration was determined using the BCA Protein Assay Reagent (Pierce Chemical Company, Rockford, Ill.). Samples containing 30 μg of proteins were boiled for 5 min in SDS sample buffer and resolved by SDS-PAGE under reducing conditions. The activation of ERK1/2 and AKT was determined by Western blot analysis using a phosphorylation-specific antibody (Cell Signaling Technology, Beverly, Mass.). The phosphorylation of IGF1R was determined by Western blotting using phosphorylation-specific antibodies (Cell Signaling Technology).

Adhesion and Binding Assays

Cell adhesion to IGF1 was measured as described (Eto et al., J Biol Chem 275(45): 34922-30, 2000). Briefly, IGF1 was coated to wells of 96-well titer plates and incubated with cells for 1 h at 37° C. in Hepes/Tyrode buffer/1 mM $MgCl_2$ buffer. Bound cells were quantified after rinsing unbound cells by phosphatase assays. ELISA-type integrin binding assay was performed as described (Saegusa et al., J Biol Chem 283(38): 26107-15, 2008). Wells of 96 well microtiter plate were coated with IGF1 and incubated with recombinant soluble αvβ3 (5 μg/ml) in the presence of 1 mM $MnCl_2$ for 1 h at room temperature. Bound αvβ3 was determined using anti-β3 mAb and peroxidase-labeled anti-mouse IgG.

Other Methods

Docking simulation and site-directed mutagenesis were performed as described (Mori et al., J Biol Chem 283(26): 18066-75, 2008).

Results

Figure 1A:
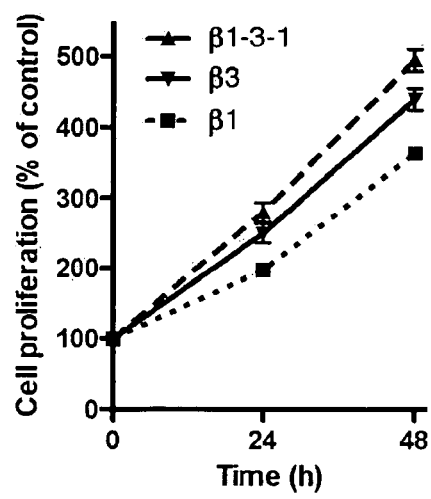
FIG. 1 $\beta 3$- and $\beta 1$-3-1-CHO cells proliferate faster than $\beta 1$-CHO cells in vitro. a) Uncloned $\beta 1$-, $\beta 3$-, or $\beta 1$-3-1-CHO cells were plated in 96-well plates (1×10⁴ cells/well), and cultured in DMEM containing 10% FBS. Cell proliferation was measured by MTS assay. Data are shown as means+/−SEM of triplicate experiments. P<0.0001 between $\beta 1$ and $\beta 3$, and between $\beta 1$ and $\beta 1$-3-1 by 2-way ANOVA. b) Cells (2.5×10⁵ cells/plate) were cultured in DMEM containing 10% FBS, and the number of cells was counted at the indicated time points. P=0.0007 between $\beta 1$ and $\beta 1$-3-1, and P=0.0005 between $\beta 1$ and $\beta 3$ by 2-way ANOVA. c) Uncloned $\beta 1$-3-1 or $\beta 1$-CHO cells were cultured with or without 10 μg/ml of anti-$\beta 1$ mAb AIIB2 in DMEM supplemented with 10% FBS for 24 h, and cell proliferation was measured by MTS assay. P=0.0033 between $\beta 1$ and $\beta 1$-3-1 and 0.0039 between $\beta 1$-3-1 and $\beta 1$-3-1+AIIB2. d) Uncloned $\beta 1$-, $\beta 3$-, or $\beta 1$-3-1-CHO cells were cultured in CHO-A serum-free medium (Invitrogen, Carlsbad, Calif.) for 48 h. Cell proliferation was measured by MTS assay. P=0.046 between $\beta 1$- and $\beta 3$-CHO cells, and 0.0382 between $\beta 1$ and $\beta 1$-3-1-CHO cells.
Figure 1B:
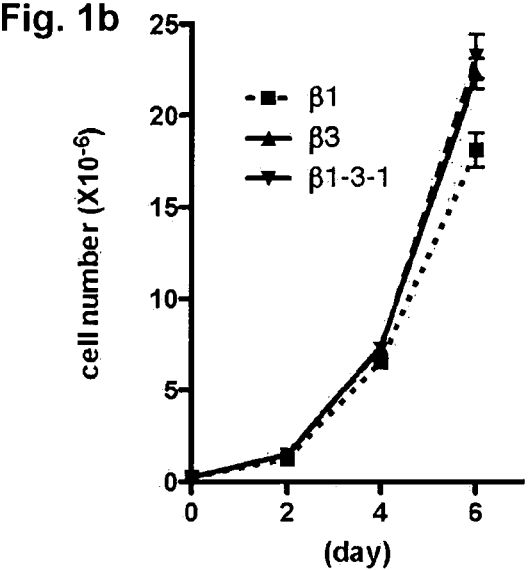

Expression of αvβ3 or αvβ1-3-1 Enhanced Cell Proliferated in Serum Free Conditions To study the role of αvβ3 in tumor progression, the rate of cell proliferation was compared between β3- and β1-CHO cells. It was discovered that β3-CHO cells proliferated faster than β1-CHO cells by MTS assay (FIG. 1a) and by counting cell numbers (FIG. 1b) in DMEM supplemented with 10% FBS. These observations are consistent with the previous reports that αvβ3 expression plays a role in tumor progression.

Figure 1C:
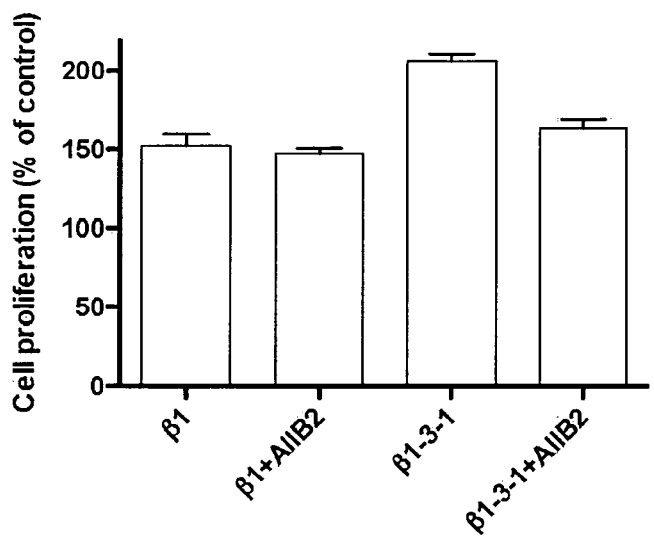

The present inventors have shown that, when the sequence CTSEQNC (SEQ ID NO:10) (residues 187-193 of β1) is replaced with the corresponding CYDMKTTC (SEQ ID NO:11) sequence of β3 (residues 177-193), the ligand specificity of αvβ1 is altered. The mutant (αvβ1-3-1), like αvβ3, recognizes fibrinogen, von Willebrand factor, and vitronectin (a gain-of-function effect) (Takagi et al., J Biol Chem 272 (32): 19794-800, 1997). This suggests that the sequence of β3 (CYDMKTTC; SEQ ID NO:11) is critical for ligand specificity of αvβ3 (Takagi et al., J Biol Chem 272(32): 19794-800, 1997). Hence the loop was designated "the specificity loop". Consistent with these observations, the loop is exposed to the surface in the ligand-binding site in the αvβ3 crystal structure (Xiong et al., Science 296(5565): 151-5, 2002). The specificity loop is diverse in sequence, and present in all β subunits except for β4, in which the loop is deleted and replaced with two remnant amino acid residues. αvβ1-3-1 also recognizes viral surface proteins (Triantafilou et al., Hum Immunol 61(5): 453-9, 2000). To test if ligand recognition by the specificity loop of αvβ3 is involved in the enhanced cell proliferation, CHO cells that express β1-3-1 mutant (designated β1-3-1-CHO cells) were studied. It was discovered that β1-3-1-CHO cells also proliferated faster than β1-CHO cells (FIGS. 1a and b), and that anti-β1 mAb AIIB2 (function blocking) inhibited the enhanced proliferation of β1-3-1-CHO cells (FIG. 1c). The sequence of β1-3-1 mutant is still more than 99% identical to the sequence of human β1, and therefore its function is blocked by anti-human β1 mAb such as AIIB2 (Takagi et al., J Biol Chem 272(32): 19794-800, 1997). These results indicate that ligand binding by the specificity loop is related to the enhanced cell proliferation of β3- and β1-3-1-CHO cells. Uncloned β3, β1, and β1-3-1-CHO cells were used for these experiments, but the results obtained were essentially the same as the results obtained with cloned β3, β1, or β1-3-1-CHO cells.

β3- or β1-3-1-CHO Cells Proliferated Faster than β1-CHO Cells in the Presence of IGF1

Figure 1D:
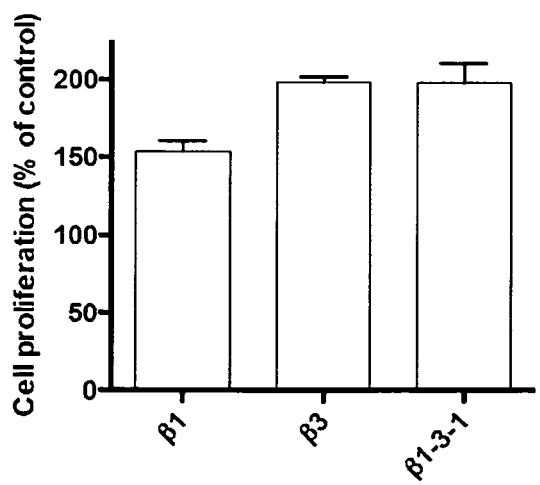
Figure 2A:
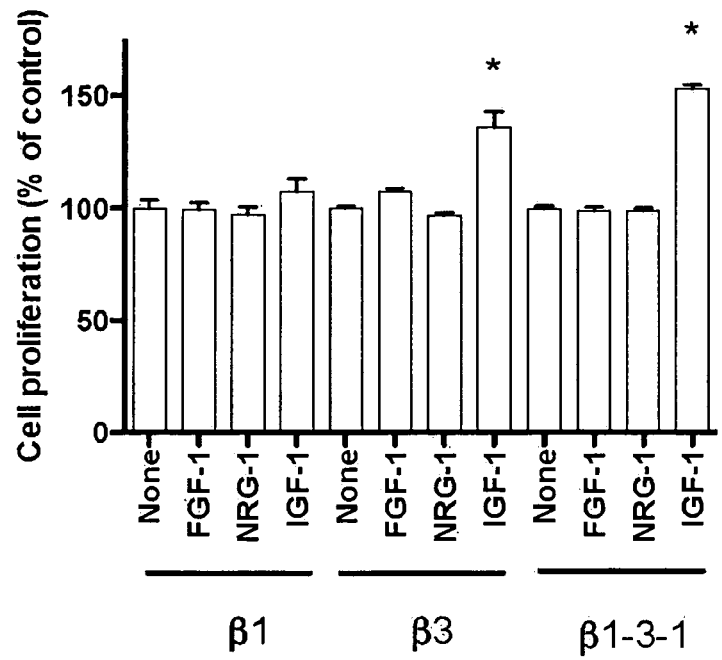
FIG. 2 Enhanced proliferation of $\beta 3$- and $\beta 1$-3-1-CHO cells in response to IGF1 compared to $\beta 1$-CHO cells. a) Effect of FGF-1, NRG-1, and IGF1 on cell proliferation. $\beta 1$-, $\beta 3$-, or $\beta 1$-3-1-CHO cells were serum-starved for 24 h, and then either treated for 24 h with 100 ng/ml of FGF-1, NRG-1, or IGF1. Cell proliferation was measured by MTS assay. Bars represent mean+/−SEM in triplicate experiments. *P=0.0065 and <0.0001 between none and IGF1 in $\beta 3$- and $\beta 1$-3-1-CHO cells, respectively. b) Dose-dependency of IGF1-induced proliferation. $\beta 1$-, $\beta 3$-, or $\beta 1$-3-1-CHO cells were serum-starved for 24 h, and then cultured with indicated concentrations of IGF1 for 24 h. Cell proliferation was determined by MTS assay. Bars represent mean+/−SEM in triplicate experiments. *P=0.0239 between 0 and 100 and P=0.0143 between 0 and 1000 in $\beta 3$-CHO cells. P=0.020 between 0 and 10, 0.002 between 0 and 100, and 0.0028 between 0 and 1000 in $\beta 1$-3-1-CHO cells.
Figure 2B:
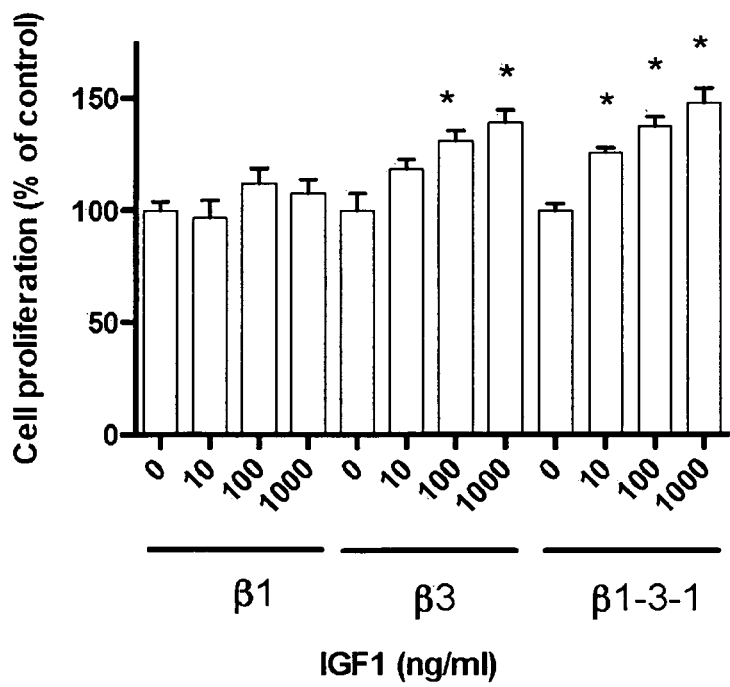

It was then tested if serum adhesive proteins are responsible for the enhanced cell proliferation of β3- or β1-3-1-CHO cells. It was discovered that the enhanced cell proliferation of β3- and β1-3-1-CHO cells occurred in commercial serum-free media for CHO cells (CHO-A) (FIG. 1d). This suggests that αvβ3 can mediate enhanced cell proliferation in the absence of serum adhesive proteins, although the contents of proprietary CHO-A media were not available. Notably, we found that β3- and β1-3-1-CHO cells proliferated better in the presence of IGF1 (100 ng/ml) in DMEM in the absence of FBS than ®1-CHO cells, but not in the presence of FGF-1 or neuregulin-1 (FIG. 2a). The effect of IGF1 on cell proliferation was dose-dependent (FIG. 2b). These results suggest that IGF1 mimics the effect of FBS in the proliferation of CHO cells.

Integrin αvβ3 Directly Interacts with IGF1

Figure 3A:
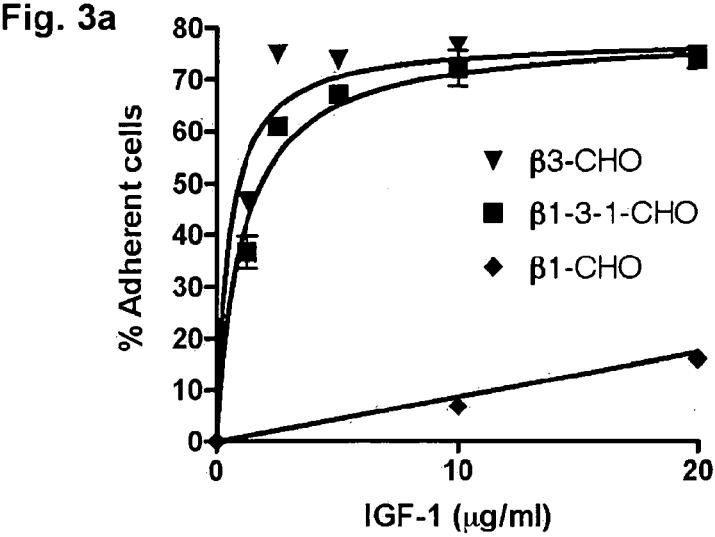
FIG. 3 Direct binding of IGF1 to $\alpha v\beta 3$ and $\alpha v\beta 1$-3-1. a) Adhesion of $\beta 3$- and $\beta 1$-3-1-CHO cells to IGF1. IGF1 was coated to wells of 96-well titer plates and incubated with cells for 1 h at 37° C. in Hepes/Tyrode buffer/1 mM $MgCl_2$ buffer. Bound cells were quantified after rinsing unbound cells. Data is shown as means+/−SEM of triplicate experiments. b) Integrin antagonists inhibit $\beta 3$ and $\beta 1$-3-1-CHO cell adhesion to IGF1. Anti $\beta 1$ mAb AIIB2 (10 μg/ml), anti-$\beta 3$ mAb 7E3 (10 and 50 μg/ml), or cyclic RGDfV peptide (an antagonist specific to $\alpha v\beta 3$, 10 μg/ml) was included in the adhesion assays using 20 μg/ml coating concentration of IGF1. *P=0.051 and 0.0017 for 7E3 at 10 and 50 μg/ml, respectively, compared to purified mouse IgG. **P=0.0008 compared to DMSO.
Figure 3B:
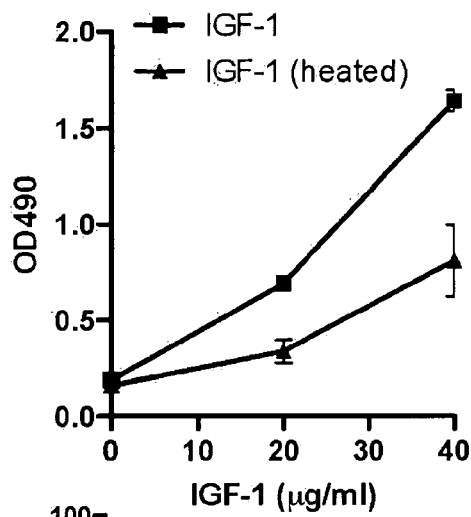
Figure 3C:
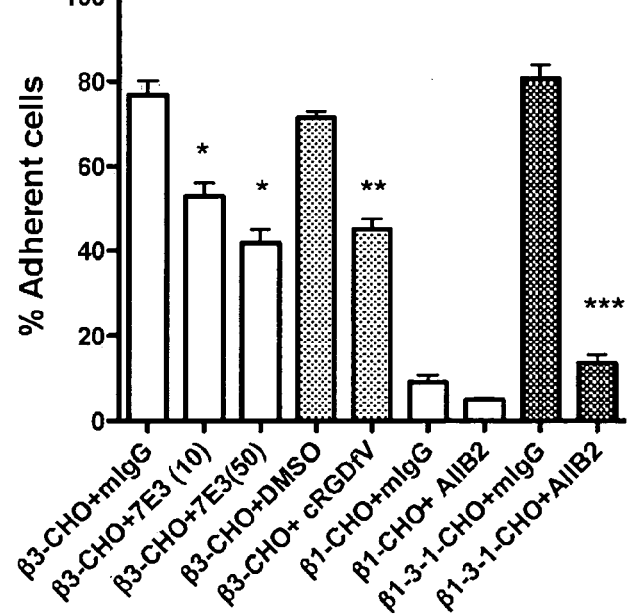

In a current model of IGF1 signaling, ligand occupancy of αvβ3 with extracellular matrix (ECM) ligands such as vitronectin plays a critical role in enhancing IGF1 signaling (Clemmons et al., Growth Horm IGF Res 17(4): 265-70, 2007). We hypothesized that IGF1 mimics the ECM ligands for αvβ3. Several different binding assays were used to study if αvβ3 interacts with IGF1 as a ligand. It was discovered that β3-CHO cells adhered to immobilized IGF1 in a dose-dependent manner while β1-CHO cells did only weakly (FIG. 3a). mAb 7E3 (anti-human β3) and cyclic RGDfV, a specific inhibitor of αvβ3 (Aumailley et al., FEBS Lett 291(1): 50-4, 1991), reduced the adhesion of β3-CHO cells to IGF1, suggesting that the interaction between αvβ3 and IGF1 was specific (FIG. 3c). In addition, soluble recombinant αvβ3 integrin bound to IGF1 in a dose dependent manner in ELISA-type assays and heat treatment of IGF1 markedly reduced the binding (FIG. 3b). This indicates that αvβ3 directly binds to IGF1 and this interaction requires proper folding of IGF1.

Surface plasmon resonance (SPR) analysis of IGF1-αvβ3 interaction was performed as described (Mori et al., J Biol Chem, 2008). Recombinant soluble αvβ3 was immobilized to a sensor chip by the standard amine coupling method. The results show a KD of 5×10-7 M, which is a reasonable affinity for integrin-ligand interaction (FIG. 9).

It has recently been reported that the specificity loop of β3 is critical for IGF1 signaling, and antibodies specific to the specificity loop blocked IGF1 signaling (through blocking ECM binding to αvβ3) (Maile et al., Mol Endocrinol 20(2): 405-13, 2006). It was discovered that β1-3-1-CHO cells bound better to IGF1 than β1-CHO cells (FIG. 3a), and mAb AIIB2 (anti-β1) reduced the adhesion of β1-3-1 CHO cells to IGF1 (FIG. 3c). These results suggest that the specificity loop of β3 is critically involved in IGF1 binding.

Localization of the Integrin-Binding Site in IGF1

To determine the biological role of the direct IGF1 binding to αvβ3, the integrin-binding site of IGF1 were identified. Docking simulation of the integrin αvβ3-IGF1 interaction using AutoDock3 was used to predict the integrin-binding site in IGF1. 50 docking simulations were performed and poses were clustered at 2 angstrom RMSD. A pose of IGF1 in cluster 1 that provided lowest docking energy (−19.4 kcal/mol) was used (FIG. 4). Our model predict that IGF1R and integrin αvβ3 bind simultaneously to IGF1 (FIG. 10). Arg residues at positions 36, 37, and 50 are located in the predicted binding surface of IGF1 to integrin. Tyr-24, Tyr-31, and Tyr-60 of IGF1 are critical for binding to IGF1R L1 domain (Bayne et al., J Biol Chem, 1990. 265(26): p. 15648-52), which are located on the side opposite to the predicted integrin-binding site (FIG. 10). The present inventors proposed a model of IGF1 signaling, in which IGF1 binds to IGF on the cell surface and integrins are recruited to the IGF1-IGF1R complex through direct binding to IGF1, making the IGFR-IGF1-integrin ternary complex. While not intended to be bound by any particular theory, it is hypothesized that the integrin-binding-defective IGF1 mutant cannot make a ternary complex and therefore defective in IGF1 signaling.

A model of IGF1-IGF1R interaction was generated according to the published model (Lou et al., Natl Acad Sci USA, 2006. 103(33): p. 12429-34) (FIG. 10). A model of IGF1R-IGF1-integrin interaction was shown in FIG. 11. This model was generated by superposing two models (IGF1-integrin interaction (FIG. 4) and IGF1-IGF1R interaction (FIG. 10). The model predicts that the C domain of IGF1 plays a role in both integrin and IGF binding and that the two receptors can simultaneously bind to IGF1 without steric hindrance.

Figure 5A:
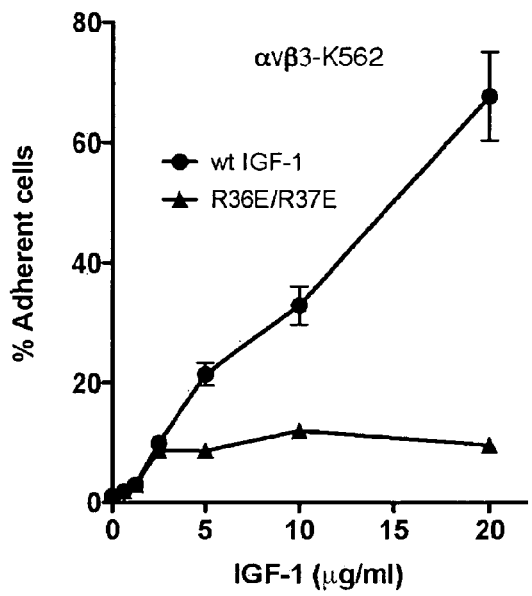
Figure 5B:
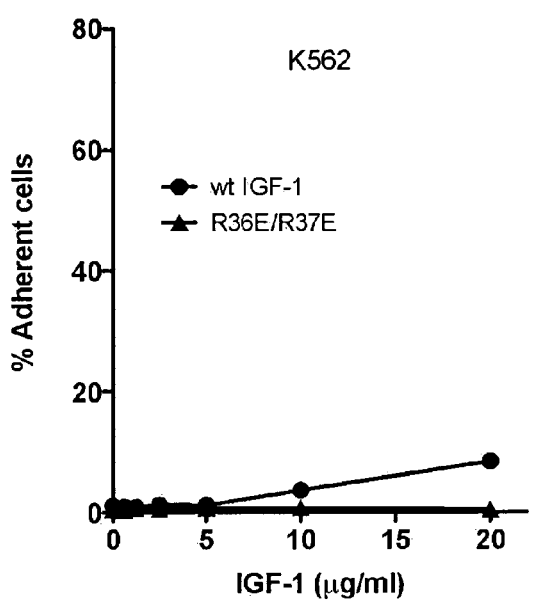
Figure 5C:
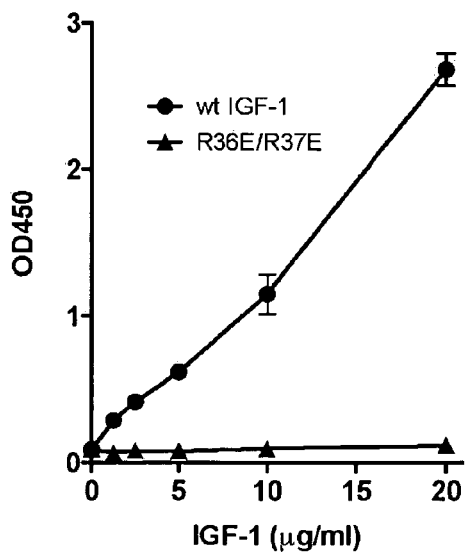

Arg residues at positions 36 and 37 within the predicted binding interface of IGF1 were mutated into Glu (designated the R36E/R37E mutant). The IGF1 mutant was defective in supporting adhesion of K562 cells that express recombinant αvβ3 (αvβ3-K562) (FIG. 5a). Mock-transfected K562 cells only weakly adhered to wt or mutant IGF1 (FIG. 5b). The R36E/R37E IGF1 bound to soluble αvβ3 at much lower levels than wt IGF1 in ELISA-type binding assays (FIG. 5c). A mutation at position 50 of IGF1 (mutant R50E) were also generated, which was shown to also markedly reduce integrin binding of IGF1 in cell adhesion assays (FIG. 12) and ELISA-type binding assays (FIG. 13). These results indicate that the Arg residues at positions 36, 37, and 50 are part of the integrin-binding interface in IGF1 as predicted by the docking simulation.

IGF1 Binds to Integrins Other than αvβ3

Figure 3D:
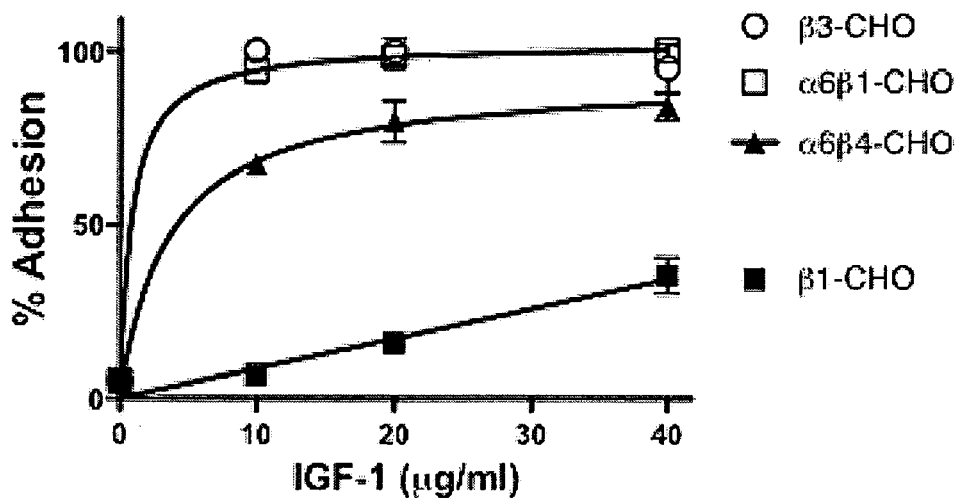
Figure 3E:
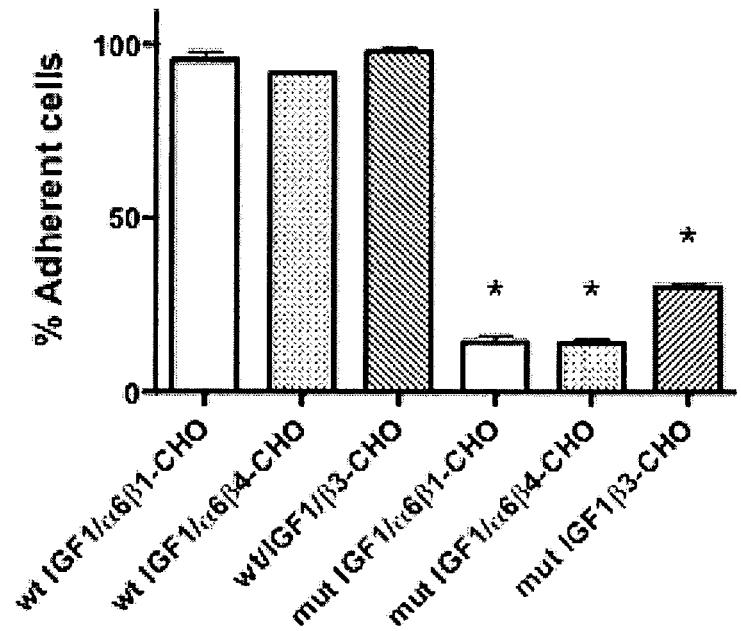

In the present invention, it was found that IGF1 binds to integrins other than αvβ3 (FIG. 3(d)). For example, IGF1 binds to α6β1 or α6β4 (FIG. 3(d)). It was also found that R36E/R37E IGF1 did not interact with α6β1 or α6β4 (*P<0.05.) (FIG. 3(e)). α6β4 is involved in tumor progression and migration.

The R36E/R37E Mutation Did not Affect the Binding of IGF1 to IGF1R

Figure 5D:
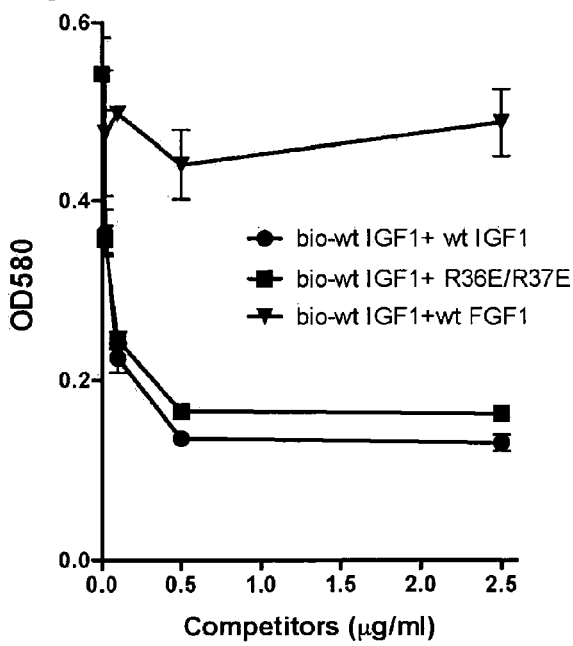

Competitive Binding Assays:

It was tested to see if the soluble IGF1 mutant compete with wt IGF1 for binding to immobilized recombinant human IGF1R (R&D systems) in an ELISA-type binding assays (FIG. 5d, and FIG. 17). It was discovered that excess wt IGF1 and IGF1 mutants (both R36E/R37E and R50E) effectively suppressed the binding of biotinylated wt IGF1 to IGF1R to the similar extent, suggesting that the IGF1 mutation did not affect the binding of IGF1 to IGF1R, and that the IGF1 mutants can bind to IGF1R. Control irrelevant ligand (wt FGF1) did not suppress the binding of wt IGF1 to IGF1R while non-labeled wt IGF1 effectively blocked the binding of biotinylated wt IGF1, suggesting that the interaction is specific. These results suggest that wt and mutant IGF1 bind to IGF1R at similar levels.

The R36E/R37E Mutant was Defective in Inducing IGF1 Intracellular Signaling

To test the effect of the R36E/R37E mutation on IGF intracellular signaling, NIH 3T3 cells that express human IGF1R (designated NIH 3T3-IGF1R) were used because non-transfected NIH 3T3 cells only generated weak signals. We found that WT IGF1 induced IGF1R phosphorylation, Shc phosphorylation, AKT phosphorylation, and ERK1/2 activation while R36E/R37E was defective in these functions (FIG. 6a). Similar results were obtained with C2C12 mouse fibroblasts (FIG. 6b). These results suggest that R36E/R37E is defective in inducing IGF1 signaling. It is likely that the direct integrin binding to IGF1 is required at the initial step (transphosphorylation of IGF1R).

Also IGF1 induced much higher levels of ERK1/2 and AKT activation in β3 and β1-3-1-CHO cells than in β1-CHO cells (FIG. 8).

The R37E/R36E Mutant of IGF-1 is Defective in Recruiting p85 of PI3 Kinase to the Type 1 IGF-1 Receptor (IGF1R)

Figure 6C:
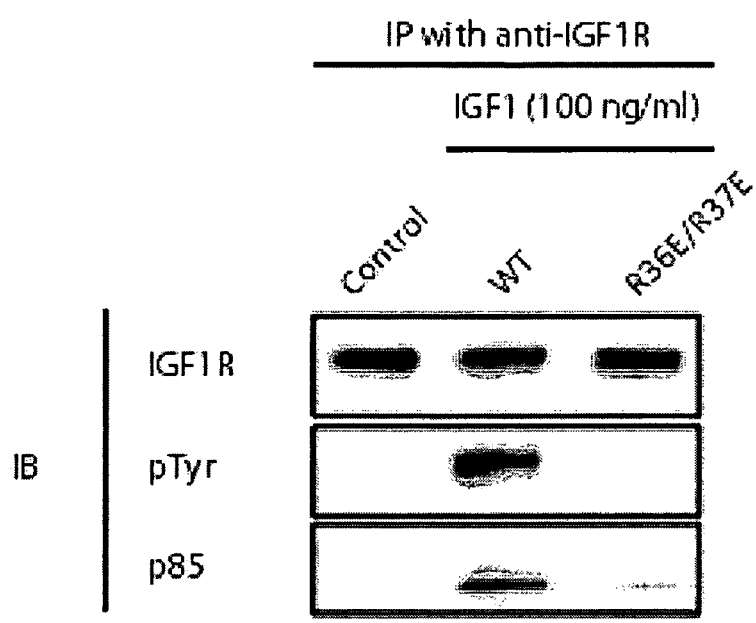

Also, R36E/R37E is defective in inducing tyrosine phosphorylation of the type 1 IGF-1 receptor (IGF1R), and inducing AKT activation and ERK1/2 activation in NIH3T3 that express human IGF1R and C2C12 cells. It is still unclear if components in IGF-1 signaling immediate downstream of IGF1R (e.g., PI3 kinase). PI3 kinase is recruited to IGF1R when IGF1R is phosphorylated upon IGF-1 binding. It was tested to see if the p85 subunit of PI3 kinase is recruited to IGF1R by R36E/R37E of IGF-1. MCF7 human breast cancer cells were stimulated with WT and R36E/R37E IGF-1 for 10 min, and immunopurified IGF1R from cell lysates and analyzed the immunopurified materials by Western blotting. It was discovered that WT IGF-1 induced tyrosine phosphorylation of IGF1R and recruitment of the p85 subunit of PI3 kinase, while R36E/R37E was defective in these functions (FIG. 6c). These results suggest that the mutant is defective in p85 recruitment to IGF1R.

The R36E/R37E was not Only Defective in Inducing Cell Proliferation, but Suppressed Cell Proliferation Induced by Wt IGF1

It was tested to see if the integrin-binding-defective mutation affects IGF1's ability to induce cell proliferation. NIH 3T3 and C2C12 cells were serum-starved, and cultured in the presence of wt or mutant IGF1 for 24 h. Wt IGF1 induced the proliferation of NIH 3T3 and C2C12 cells (FIGS. 7a and 7b), while R36E/R37E did not. NIH 3T3 cells express endogenous IGF1R and integrin αvβ3. These results suggest that R36E/R37E was defective in inducing cell proliferation, which is consistent with its defect in inducing intracellular signaling. It was also showed that the IGF1 mutants were defective in inducing cell proliferation in β3-CHO cells (FIG. 15). This suggests that the direct integrin binding to IGF1 plays a critical role in IGF1 signaling. Furthermore, we demonstrated that excess IGF-1 mutants suppressed cell proliferation induced by wt IGF-1 (FIG. 16). This is a dominant-negative effect by definition. Notably it was discovered that excess R36E/R37E suppressed cell proliferation induced by wt IGF1 in NIH 3T3 and C2C12 cells (FIGS. 7c and 7d). This finding suggest that R36E/R37E is a dominant-negative mutant by definition. This is consistent with a model that IGF1 signaling requires two receptors (IGF1R and integrins).

Suppression of Tumor Growth In Vivo by a Dominant-Negative IGF1 Mutant.

Furthermore, it was demonstrated that intraperitoneal injection of one of the IGF1 mutants (R36E/R37E) effectively suppressed the growth and lung metastasis of Met-1 highly metastatic breast cancer in mouse (FIG. 17). Met-1 cancer is a model of a highly metastatic breast cancer.

The Dominant-Negative IGF1 Mutant Suppressed Tumor Growth and Metastasis In Vivo at a Low Dose (100 ng/mouse/day).

It was tested to see whether intraperitoneal injection of the R36E/R37E IGF1 mutant affects tumor growth in vivo in a small-scale experiment. Met-1 (a highly metastatic mouse mammary tumor) (Guy et al., Mol Cell Biol, 1992. 12(3): p. 954-6137; Cheung et al., Int J Oncol, 1997. 11: p. 69-77) (2 mm×2 mm×2 mm) was transplanted to nude mice and intraperitoneally injected the mutant at a very low dose (100 ng/mouse/day, 5 days/week). R36E/R37E almost completely suppressed tumor growth at this low dose (FIG. 18). This suggests that R36E/R37E effectively suppressed tumor growth in vivo. Also, it was discovered that mice treated with the IGF1 mutant did not have lung metastasis while all of the mice treated with PBS only had multiple metastatic foci. These results suggest that the proposed in vivo studies on the suppression of tumor growth using transgenic mouse models are feasible.

DISCUSSION

In the present study it was established that expression of αvβ3 enhanced proliferation of CHO cells in the presence of serum. The ligand binding specificity of αvβ3 through the specificity loop plays a critical role in this function. Notably αvβ3 enhanced cell proliferation in serum-free media if IGF1 is present, and the specificity loop is involved in this function as well. These results indicate that IGF1 mediates enhanced proliferation of cancer cells that express αvβ3.

It was demonstrated that αvβ3 interacts directly with IGF1 in several binding assays. This interaction is specific since anti-β3 mAb 7E3 and cyclic RGDfV peptide blocked the interaction. The epitopes of 7E3 have been previously mapped in the ligand-binding site of β3 (Puzon-McLaughlin et al., J Biol Chem 275(11): 7795-802, 2000; Artoni et al., Proc Natl Acad Sci USA 101(36): 13114-20, 2004). The interaction involved the specific loop of the β3 subunit using the β1-3-1 mutant. Anti-β1 mAb AIIB2 effectively blocked IGF1 binding to αvβ1-3-1. The epitope for mAb AIIB2 has been mapped in the non-ligand-binding site and it appears that this mAb changes the conformation of the ligand-binding site of β1 integrins (Takada and Puzon, J Biol Chem 268(23): 17597-601, 1993). It has been reported that the β3 mutant, in which the specificity loop of β3 is mutated, suppressed IGF1 signaling and antibodies specific to the specificity loop of β3 blocked IGF1 signaling (Maile et al., Mol Endocrinol 20(2): 405-13, 2006). Taken together it is highly likely that IGF1 directly interacts with the specificity loop of β3.

The integrin-binding site in IGF1 was identified by docking simulation and mutagenesis. The R36E/R37E mutation within the C domain (residues 30-41) effectively blocked IGF1-αvβ3 interaction, but did not affect the IGF1 binding to IGF1R. Notably, the mutant was defective in inducing cell proliferation, IGF1R phosphorylation, AKT activation, and ERK1/2 activation. These results suggest that the ability of IGF1 to directly interact with integrins is critical for IGF signaling.

It has been reported that replacing the C-loop of IGF1 with 4 Gly residues much reduced the binding affinity to IGF1R (Bayne et al. J Biol Chem 264(19): 11004-8, 1989), suggesting that the C-loop is involved in IGF1/IGF1R interaction. Three Tyr residues at positions 24, 31, and 61 of IGF1 are critical for IGF1R binding since mutating these residues individually significantly reduced the affinity to IGF1R (Bayne et al., J Biol Chem 265(26): 15648-52, 1990). IGF1 binds to the hydrophobic patch in the L1 domain of IGF1R and the three Tyr residues are expected to interact with the L1 domain (Garrett et al., Nature 394(6691): 395-9, 1998). We generated a model in which the L1 domain of IGFR1 and IGF1 interact according to the docking model of insulin-insulin receptor interaction (Lou et al., Proc Natl Acad Sci USA 103(33): 12429-34, 2006). It should be noted that the three Tyr residues in the C-loop is located on the opposite side of the Arg-36 and Arg-37 residues that are involved in integrin binding. This model predicts that integrin and IGF1R binding sites are distinct and there will be no steric hindrance between integrin and the L1 domain if they bind to IGF1 simultaneously.

The present inventors propose that soluble IGF1 preferentially binds to IGF1R on the cell surface (since IGF1 has a higher affinity to IGF than to integrins), and, if this is the case, $\alpha v\beta 3$ may bind to receptor-bound IGF1. Taken together, the present results generate an alternative hypothesis of the role of integrin $\alpha v\beta 3$ in IGF1 signaling, in which IGF1 directly binds to integrin $\alpha v\beta 3$ on the cell surface and this interaction plays a role in IGF1 signaling. Because antagonists to $\alpha v\beta 3$ are expected to block both $\alpha v\beta 3$-extracellular matrix and $\alpha v\beta 3$-IGF1 interactions, it is unclear whether the reported inhibition of IGF1 signaling by $\alpha v\beta 3$ antagonists is due to the inhibition of the $\alpha v\beta 3$-IGF1 interaction and/or the $\alpha v\beta 3$-extracellular matrix interaction. The IGF1 mutant is expected to specifically block IGF1-integrin interaction without effecting ECM-integrin interaction.

Notably excess R36E/R37E suppressed cell proliferation induced by WT IGF1, suggesting that it is a dominant-negative mutant by definition. This observation is consistent with a model in which both IGF1R and integrins have to bind to IGF1 during IGF1 signaling. Because R36E/R37E was defective in inducing tyrosine phosphorylation of IGF1R, we believe that the direct binding of integrins to IGF1 is involved in the initial step of IGF11 signaling. As such, IGF1-integrin interaction is a novel therapeutic target and R36E/R37E, as well as other inhibitors of IGF1-integrin binding (such as anti-$\beta 3$ mAb 7E3 and cyclic RGDfV peptide), can be useful as a therapeutic.

Example 2

The Effect of the Dominant-Negative IGF1 Mutants on IGF Signaling

Methods.

Preparation of Recombinant IGF1 in *E. coli*.

A fragment of cDNA encoding human IGF1 is subcloned into the Nco I/Xho I site of PET28a vector. IGF1 is synthesized in bacteria BL-21 as an insoluble protein using the IGF1 expression construct, purified using Ni-NTA affinity chromatography under denaturing conditions, and refolded in vitro.

Docking simulation of integrin-IGF1 interaction is performed as previously described (Legge et al., Proteins, 2002. 48(2): p. 151-60). Site-directed mutagenesis, adhesion assays, and binding of soluble integrin to immobilized ligand is performed as described (Mori et al., J Biol Chem, 2008). Biacore 3000 is used for surface plasmon resonance (SPR) for measuring affinity of IGF mutants to IGF1R. Western blotting is used to determine IGF1R phosphorylation, ERK1/2 activation, and Akt phosphorylation using commercially available antibodies against phosphorylated proteins as described (Mori et al., J Biol Chem, 2008). Total IGF1R, ERK1/2, and Akt proteins is measured using commercially available antibodies specific to these proteins. Adhesion and binding assays is performed as described (Mori et al., J Biol Chem, 2008).

NIH 3T3 that Express Human IGF1R.

Human IGF1R is transfected in pZEM mammalian expression vector (Slaaby et al., J Biol Chem, 2006. 281(36): p. 25869-74). pZEM has a metallothionein-inducible promoter, but we use base-line expression and do not induce it with $Cu^{2+}$ to avoid over-expression of IGF1R.

The IGF-I mutants are examined for binding to transmembrane form IGF1R on the cell surface. Wt IGF1 is labeled with $^{125}$I or fluorescent dye (e.g., FITC). IGF1 mutants are examiner to see whether they compete with wt IGF1 for binding to IGF1R (e.g., on NIH 3T3 cells). Bound IGF is detected by using gamma counter or flow cytometry. Ki is calculated from these experiments.

Surface plasmon resonance (SPR) is used for measuring affinity of IGF mutants to IGF1R according to procedures described recently (Mori et al., J Biol Chem, 20085; Saegusa et al., J Biol Chem, 2008. 283(38): p. 26107-15). Recombinant soluble IGF1R (commercially available from R&D systems) is immobilized to a sensor chip by a standard amine coupling method, and monitor the binding and dissociation of wt or mutant IGF1 in a solution phase at different IGF concentrations. The binding constants is calculated from the binding curve.

The results indicate that integrin-binding-defective IGF1 mutants compete with wt IGF1 for binding to IGF1R on the cell surface, and thus the mutants are competitive inhibitors of IGF signaling. This confirms the results obtained by SPR using soluble form of IGF1R.

In addition, the integrin-binding-defective mutants are examined to see if they affect IGF1 signaling in vitro, including Akt and ERK1/2 activation, IGF1R phosphorylation, cell proliferation, and integrin $\beta 3$ tail phosphorylation in NIH 3T3 or NIH 3T3 cells that express human IGF1R (NIH 3T3-IGF1R).

Finally, CHO or K562 erythroleukemia cells that express different recombinant human integrins (e.g., $\alpha 1$, $\alpha 2$, $\alpha 4$, $\alpha M\beta 2$, and $\alpha L\beta 2$) are used to test which integrins bind to IGF1. Antibodies or small-molecular weight antagonists specific to individual integrins are used to show the specificity to integrins.

In this experiment, experiments are carried out to identify where the dominant-negative IGF1 mutants are defective in IGF1 signaling. The direct binding of integrin to IGF is examined to see if it is required for IGF1R phosphorylation. It has been proposed that "ligand occupancy" of integrin $\alpha v\beta 3$ enhances IGF signaling (Clemmons et al., Growth Horm IGF Res, 2007. 17(4): p. 265-70). In this experiment, the role of integrins in IGF signaling is examined to see if integrins are involved in the initial IGF1R activation.

Example 3

Identification of the IGF1R-IGF1-Integrin Ternary Complex

Methods.

Co-Precipitation from Cell Lysates:

NIH 3T3 cells that overexpress IGF1R (NIH 3T3-IGF1R cells) are incubated with wt IGF or the integrin-binding-defective IGF1 mutants at saturating conditions (e.g., 100 ng/ml) and the complex with anti-IGF1R is precipitated from detergent cell lysates. Integrin $\beta 3$ is detected by Western blotting with specific antibodies to $\beta 3$. The complex is precipitated with anti-$\beta 3$ antibody and the immuno-purified materials is analyzed by western blotting with anti-IGF1R antibody.

Co-Precipitation of Soluble IGF and Soluble Integrin:

IGF1 binds to IGF1R at a higher affinity than to integrins. Wt IGF1 is incubated with the IGF1R and then soluble αvβ3 (6His (SEQ ID NO:9) tagged) in solution in the presence of 1 mM Mn2+ (to activate integrins). The complex is recovered by incubating with Ni-NTA-Sepharose. Proteins recovered are analyzed by Western blotting with an anti-6His (SEQ ID NO:9) antibody, anti-IGF1R mAb (commercially available), or control irrelevant antibodies. The IGF1 mutants (integrin-binding-defective) are used as controls. Alternatively, 6His (SEQ ID NO:9) tagged IGF1 is immobilized to Ni-NTA-Sepharose, and is incubated with IGF1R. Unbound IGF1R is washed away. The complex is then incubated with soluble αvβ3. The recovered protein is analyzed by Western blotting. Integrin-binding-defective IGF1 mutants is used. The results indicate that integrin binding to IGF1 is required for the ternary complex. IGF1R-binding-defective IGF mutants (in which Tyr residues at positions 24, 31, and/or 60 are mutated) are used as a negative control.

The mutations in the integrin-binding site of IGF1 block integrin binding and IGF1 signaling although these mutants still bind to IGF1R. It is predicted that the direct integrin binding to IGF is required for IGF signaling in addition to the binding to IGF1R. If this is the case, it is possible that IGF1 binds to IGF1R and integrins simultaneously. The model (FIGS. 4, 10-11) also predicts that the integrin-binding site is exposed in IGF1 when IGF1 binds to IGF1R.

NIH 3T3-IGF1R cells are incubated with wt IGF1 to generate cell lysates. The integrin-IGF1 complex is immunoprecipitated from the cell lysates using antibodies specific to integrin β3, and checked to see if this complex contains IGF1R. The immunoprecipitated materials are analyzed by Western blotting with antibodies specific to IGF1R. As a reciprocal experiment, the IGF1R-IGF1 complex is immunoprecipitated from the cell lysates using antibodies specific to IGF1R. The immunoprecipitated materials are analyzed by Western blotting with antibodies specific to integrin β3. Integrin-binding-defective IGF1 mutants are then tested to see whether the mutant can induce the complex formation. These experiments will tell us if IGF1, IGF1R, and integrin αvβ3 make a ternary complex and if the direct binding of integrins to IGF1 is required for the ternary complex formation. If this is really the case; the integrin-binding-defective IGF1 mutants do not form the ternary complex.

Alternatively, soluble αvβ3, soluble recombinant IGF1R (available from R&D systems) and IGF1 are examined to see if they form an IGF/IGF1R/integrin complex. Dominant-negative IGF1 mutants are used to determine if the integrin-binding-defective IGF1 mutant is able to generate the ternary complex. IGF1R-binding-defective IGF1 mutants, in which Tyr residues at positions 24, 31, and 60 in IGF1 that are critical for IGF1R binding (Lou et al., Proc Natl Acad Sci USA, 2006. 103(33): p. 12429-34) are mutated, are used as a negative control.

It is expected that wt IGF1 induces the formation of the IGF-IGF1R-αvβ3 complex, but the IGF1 that have mutations in the integrin-binding or IGF1R-binding site of IGF1 do not. If both wt and integrin-binding-defective mutants of IGF1 bind to IGF1R in a similar manner, the ability of IGF1 to bind to integrins may be critical for the ternary complex formation and subsequent signaling.

By incubating cells with wt IGF1 for a different duration (e.g., 10 min-3 h), the time-course of the role of integrins in IGF signaling can be detected. The direct binding of integrins to IGF1 is expected to be required for the very early stage of IGF signaling.

It has been reported that integrins associate with several signaling molecules (Takada et al., Genome Biol, 2007. 8(5): p. 215). It is possible that the IGF1R-IGF-integrin complex from total cell lysates may contain these components (e.g., Shc). Other components can be detected by staining SDS gels (e.g., silver staining) or by Western blotting with antibodies specific to the proteins (e.g., anti-Shc).

Example 4

Identify Relative Contribution of ECM-Integrin Interaction and IGF-Integrin Interaction to IGF Signaling It has been proposed that cell adhesion to fibronectin is required for FGF2-induced sustained ERK1/2 signaling that supports cell cycle progression using NIH 3T3 cells that express exogenous human α5β1 (Welsh et al., Nat Cell Biol, 2001. 3(11): p. 950-7). However, it has also been reported that adhesion of NIH 3T3 cells to fibronectin selectively enhanced ERK1/2 signaling elicited by EGF, but has no effect on FGF2- or PDGF-mediated ERK1/2 activation (Galownia et al., J Biol Chem, 2007. 282(30): p. 21758-66). The effect of integrin-binding-defective IGF mutants is tested using adherent NIH 3T3 cells that can interact with ECM (e.g., vitronectin and fibronectin) on tissue culture plates. Cell adhesion is blocked using hydrogel poly-HEMA [Poly(hydroxyethyl methacrylic)]-coated surfaces to examine whether this blocking affects IGF1 signaling and the effect of dominant-negative IGF1 mutants on IGF signaling.

The plastic dish is coated with poly-HEMA as described (Galownia et al., J Biol Chem, 2007. 282(30): p. 21758-66). This treatment will block cell adhesion and keep cells in suspension. Serum-starved NIH 3T3 cells are seeded, and then stimulated with wt IGF1 or dominant-negative IGF1 mutants (5 ng/ml) in DMEM with 0.4% FCS. As a control, serum-starved cells are seeded in regular tissue-culture dish, or fibronectin-coated dish, and then stimulated with wt IGF1 or dominant-negative IGF1 mutants as described above. Cells are harvested after 15 min, 1 h, 3 h, and 6 h, and the cell lysates are analyzed by western blotting with antibodies specific to ERK1/2 and other signaling molecules (phosphorylated and total) as described above.

To assess the effect of poly-HEMA treatment on apoptosis due to Anoikis, levels of caspase 3 activation (cleavage) are measured by western blotting with specific antibodies to cleaved caspase 3. It is not likely that suspended NIH 3T3 cells undergoes extensive apoptosis since it has been reported that NIH 3T3 cells are viable up to 5 h in poly-HEMA treatment (Galownia et al., J Biol Chem, 2007. 282(30): p. 21758-66).

It is expected that IGF1 induces ERK1/2 activation in both regular tissue culture dish or poly HEMA-coated surfaces at comparable levels. If this is the case, these results are consistent with a previous report that FGF2 signaling did not require cell adhesion to ECM (Galownia et al., J Biol Chem, 2007. 282(30): p. 21758-66). It is expected that dominant-negative IGF1 mutants do not induce IGF signaling in both surface conditions (ECM-coated and poly-HEMA-coated), and that the integrin-IGF interaction is independent of integrin-ECM interaction.

Example 5

The Dominant-Negative IGF1 Mutants Suppress Tumor Growth and Angiogenesis in a Genetically Engineered Mouse (GEM) Breast Cancer Model The MMTV-PyV-mT mouse is a well-established genetically engineered mouse (GEM) model of breast cancer.

Transplantable Met-1 and MIN-O derive from this transgenic mouse, and thus they have the same genetic background. Tg(MMTV-PyV-mT) model mimic the biology of human breast cancer (Maglione et al., Cancer Res, 2001. 61(22): p. 8298-305). The Tg(MMTV-PyV-mT) mammary fat pad develops multifocal tumors at 100% penetrance with multistage development of mammary invasive carcinoma (atypical, hyperplastic, invasive, and metastatic). Although PyV-mT is not an endogenous oncogene, it acts as a molecular surrogate for ErbB2, an oncogene associated with breast cancer, to activate ErbB2-related signaling pathways, including Phosphoinositide-3-kinase (PI3K)/Akt pathway (Dilworth S. M., Nat Rev Cancer, 2002. 2(12): p. 951-6). Tg(MMTV-PyV-mT) tumors have high PI3K activity (Webster et al., Mol Cell Biol, 1998. 18(4): p. 2344-59). The molecular biology and histopathology of PyV-mT mouse mammary lesions also strongly resemble human breast cancer (Namba et al., Clin Cancer Res, 2006. 12(8): p. 2613-21; Rosner et al., Am J Pathol, 2002. 161(3): p. 1087-97).

Met-1 cancer is a model of a highly metastatic breast cancer, and MIN-O precancerous lesion is a model of ductal carcinoma-in-situ (DCIS). These transplantable lesions originated from Tg(MMTV-PyV-mT) female mammary fat pads (Borowsky et al., Clin Exp Metastasis, 2005. 22(1): p. 47-59; Maglione et al., Mol Cancer Ther, 2004. 3(8): p. 941-53) and have high levels of Akt activation.

Methods

Tg(MMTV-PyV-mT) mice is bred and maintained at UC Davis.

Immunohistochemistry:

The tissues is fixed in 10% formalin for immunohistochemistry. Anti-caspase-3 (activated) (Promega) is used as a marker of apoptosis and anti-Ki67 as a marker for cell proliferation. Anti-CD31 is used to detect vascular region.

micro-PET Study:

All animals are imaged by micro-positron emission tomography (PET) immediately before the beginning of the IGF1 treatment and at 7th and 14th day of the treatment. Micro-PET imaging are carried out with the help of the Center for Molecular and Genomic Imaging at UC Davis. Animals are scanned on a dedicated small-animal PET scanner (micro-PET Focus system) using the glucose analogue 2-[$^{18}$F]fluoro-deoxy-D-glucose. For the scanning protocol animals are anesthetized, injected with 200 to 300 µCi 2-[$^{18}$F]fluoro-deoxy-D-glucose, and held 30 min for biodistribution of the tracer before commencing with a 30-minute scan. Tumor volume are calculated using 3D-Image analysis software.

a) In Vitro Met-1 Studies

Previously it has been shown that one of the dominant-negative IGF1 mutants suppressed the growth of highly metastatic Met-1 cells in vivo in a small-scale experiment. Here the effect of dominant-negative IGF1 mutants on the IGF signaling in Met-1 cells in vitro is studied. The Met-1 cells is maintained in DMEM supplemented with 10% fetal calf serum as described (Borowsky et al., Clin Exp Metastasis, 2005. 22(1): p. 47-59; Maglione et al., Mol Cancer Ther, 2004. 3(8): p. 941-53). The cells are serum starved in DMEM without FCS and stimulated with wt IGF1, dominant-negative IGF1, or vehicle only, for 15 min to 6 h. It is then tested to see if dominant-negative IGF1 affects components of the IGF signaling pathway as seen in NIH3T3 cells, such as including IGF1R phosphorylation, ERK1/2 activation, phospho-AKT, and PI3K, by western blotting with specific antibodies. It has been generally accepted that malignant cancer cells have autocrine growth factor loops. This might be the case in Met-1 cells. The expression profiles of IGFs and IGF1R are available from recent gene chip analysis of Met-1 cells (Borowsky et al., Clin Exp Metastasis, 2005. 22(1): p. 47-59). MTS assays are used to test if IGF1 or dominant-negative IGF1 affects proliferation of Met-1 cells in vitro.

It is expected that dominant-negative IGF1 suppresses proliferation of Met-1 in vitro.

b) In Vivo Met-1 Tumor Studies

Met-1 tumor is transplanted to fat pads of syngeneic FVB mouse. With 0.25% trypsin 70-80% confluent cells are harvested and washed with PBS. Vital cells are counted using trypan blue and suspended to a final concentration in PBS. For mammary fat pad injection, bilateral inguinal (Shimaoka et al., Cell, 2003. 112(1): p. 99-111) mammary fat pads of FVB/N female mice are exposed and $10^6$ cells/50 µl per fat pad are injected using a 30-gauge needle. Wt IGF1 and dominant-negative IGF1 mutants treatment are started when the transplanted Met-1 tumors became palpable at 14 days post-transplantation. Animals are treated at 100 ng/mouse/day doses for 21 days (eight animals per group) by intraperitoneal injection. This dose worked in our preliminary studies. During the treatment, tumor size is measured in two dimensions using calipers until the vehicle treated control tumors reached 1.5 cm in diameter. Tumor size is calculated using the formula (length×width$^2$)/2. At the end of the study, small pieces of the tumors are flash frozen and the remaining tumor tissue are fixed in 10% formalin. It has been well established that Met-1 tumors generate lung metastasis (100%). The number of lung metastasis is counted.

It is expected that dominant-negative IGF1 mutants reduce lung metastasis.

c) In Vivo MIN-O Studies

To study the effect of the IGF1 mutants on the premalignant cancer, transplantable mammary intraepithelial neoplasia-outgrowth (MIN-O) tissue lines derived from hyperplastic mammary lesions in young Tg(MMTV-PyV-mT) females is used. The resulting lesions mimic the biological behavior, molecular biology, and histopathology of human ductal carcinoma in situ. One-mm$^3$ pieces of the 8w-BMINO tissues are transplanted to gland-cleared no. 4 mammary fat pads of 3-week-old FVB females bilaterally. See detailed description of experimental procedures in Maglione et al., Mol Cancer Ther, 2004. 3(8): p. 941-53.

The IGF1 mutants (100 ng/day/mouse) are intraperitoneally injected to FVB mice that has been transplanted with MIN-O (eight animals per group) 5 days a week for 4 weeks. This dose worked in our preliminary studies. Treatment starts 7 days after transplantation and continues for 35 days. The size of MIN-O is measured as an indicator of growth. Pathological analysis of tissue sections as an indicator of tumor progression is then used to determine if MIN-O develops to tumor by. The effects of dominant-negative IGF1 mutants and wt IGF1 in vivo are evaluated using the small-animal positron emission tomography (PET) imaging technique previously shown to discriminate premalignant from malignant tissue in the MIN-O model (Abbey et al., Proc Natl Acad Sci USA, 2004. 101(31): p. 11438-43).

Analysis of the IGF1 Mutants on IGF Signaling in MIN-O:

Because it is difficult to culture MIN-O in vitro, mice bearing MIN-O are treated for a short time period (e.g., 7-day treatment starting at day 7) and tested to see if dominant-negative IGF1 affects intracellular signaling. MIN-O tissues are homogenized in lysis buffer (10 mM Tris buffer pH 7.6 containing protease inhibitor, caspase inhibitor, phosphatase inhibitor) with a Dounce homogenizer. The lysates are analyzed by Western blotting with antibodies specific to phosphorylated ERK1/2, AKT, and PI3K.

d) Tg(MMTV-PyV-mT) Transgenic Mice Studies

For testing the effect of dominant-negative IGF1 mutants on the initiation of tumorigenesis, dominant-negative IGF1 mutants or wt IGF1 are injected to mice (100 ng/mouse, intraperitoneal injection) at 2-3 weeks of age, probably twice a week. For testing the effect of dominant-negative IGF1 on the development of tumors, dominant-negative IGF1 mutants or wt IGF1 are injected after tumors become palpable (4-5 weeks of age). The size of the tumor is measured every week using calipers. As controls dominant-negative IGF1 mutants, wt IGF1, or vehicle only are injected into normal mice to test whether they affect the normal development of mammary gland. The effect on gland development during puberty or pregnancy is studied. Tumors are visualized using 2-[18F] fluoro-deoxy-D-glucose and PET imaging. Vehicle only was injected as a control.

Dominant-negative IGF1 mutants affect tumor cells and stromal cells, including endothelial cells and fibroblasts, and immune-competent cells that infiltrate the tumor. The levels of infiltrating cells are quantified by staining the tissue section with specific markers (e.g., F4/80 as a macrophage marker). The levels of angiogenesis are quantified by staining vascular markers (e.g., CD31) in tissue sections by immunohistochemistry. At the end of the experiment, "tumor burden" is evaluated. All ten fat pads were dissected, and weighed or made whole mounts of the fat pads. They were photographed. Total area occupied was calculated.

The effect of dominant-negative IGF1 and wt IGF1 on tumor initiation and development is established. The effect of dominant-negative IGF1 mutants on leukocyte infiltration, and angiogenesis is determined by immunohistochemistry of tissue sections. Dominant-negative IGF1 mutants do not dramatically affect development of mammary glands or other tissues in normal mice.

The transgenic model of cancer is appropriate for evaluating the potential of the anti-cancer activity of IGF1 mutants, in vivo imaging of the distribution of the IGF1 mutants in different stages of tumor development is performed to determine the biodistribution and half-life of the injected proteins.

All patents, patent applications, and other publications, including GenBank Accession Numbers, cited in this application are incorporated by reference in the entirety for all purposes.

What is claimed is:

1. An isolated polypeptide comprising the amino acid sequence of SEQ ID NO:1, with both of the Arg residues at positions 36 and 37 of SEQ ID NO:1 substituted with Glu, or with the Arg residue at position 50 of SEQ ID NO:1 is substituted with Glu.

2. A composition comprising the polypeptide of claim 1 and a pharmaceutically acceptable excipient.

3. The composition of claim 2, wherein the polypeptide is IGF1 mutant R36E/R37E.

4. The composition of claim 2, wherein the polypeptide is IGF1 mutant R50E.

5. A kit for inhibiting IGF1 signaling, comprising the composition of claim 2.

6. A method for inhibiting IGF1 signaling in a cell, comprising the step of contacting the cell with an effective amount of the polypeptide of claim 1.

7. The method of claim 6, wherein the inhibitor is IGF1 mutant R36E/R37E.

8. The method of claim 6, wherein the inhibitor is IGF1 mutant R50E.

9. The method of claim 6, wherein the cell is within a patient's body.

10. The method of claim 9, wherein the contacting step is performed by intravenous, intraperitoneal, or intratumor injection.

* * * * *

SEQUENCE LISTING

```
<160> NUMBER OF SEQ ID NOS: 11

<210> SEQ ID NO 1
<211> LENGTH: 70
<212> TYPE: PRT
<213> ORGANISM: Homo sapiens
<220> FEATURE:
<223> OTHER INFORMATION: human mature wild type insulin-like growth
      factor 1 (IGF1, IGF-1A, IGFBP1), somatomedin-C, mechano
      growth factor (MGF)

<400> SEQUENCE: 1

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 2
<211> LENGTH: 35
<212> TYPE: DNA
<213> ORGANISM: Artificial Sequence
<220> FEATURE:
<223> OTHER INFORMATION: synthetic oligonucleotide PCR primer 1 for
      amplification of cDNA fragment encoding IGF1

<400> SEQUENCE: 2
ccgacgcatc catggctgga ccggagacgc tctgc                              35

<210> SEQ ID NO 3
<211> LENGTH: 33
<212> TYPE: DNA
<213> ORGANISM: Artificial Sequence
<220> FEATURE:
<223> OTHER INFORMATION: synthetic oligonucleotide PCR primer 2 for
      amplification of cDNA fragment encoding IGF1
```

-continued

<400> SEQUENCE: 3
gtggtgctcg agagctgact tggcaggctt gag    33

<210> SEQ ID NO 4
<211> LENGTH: 79
<212> TYPE: PRT
<213> ORGANISM: Artificial Sequence
<220> FEATURE:
<223> OTHER INFORMATION: synthetic wild type IGF1 with C-terminal
      6His-tag

<400> SEQUENCE: 4

Met Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr Gly Tyr
            20                  25                  30

Gly Ser Ser Ser Arg Arg Ala Pro Gln Thr Gly Ile Val Asp Glu Cys
        35                  40                  45

Cys Phe Arg Ser Cys Asp Leu Arg Arg Leu Glu Met Tyr Cys Ala Pro
    50                  55                  60

Leu Lys Pro Ala Lys Ser Ala Leu Glu His His His His His
65                  70                  75

<210> SEQ ID NO 5
<211> LENGTH: 79
<212> TYPE: PRT
<213> ORGANISM: Artificial Sequence
<220> FEATURE:
<223> OTHER INFORMATION: synthetic IGF1 R36E/R37E mutant with C-terminal
      6His-tag

<400> SEQUENCE: 5

Met Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr Gly Tyr
            20                  25                  30

Gly Ser Ser Ser Glu Glu Ala Pro Gln Thr Gly Ile Val Asp Glu Cys
        35                  40                  45

Cys Phe Arg Ser Cys Asp Leu Arg Arg Leu Glu Met Tyr Cys Ala Pro
    50                  55                  60

Leu Lys Pro Ala Lys Ser Ala Leu Glu His His His His His
65                  70                  75

<210> SEQ ID NO 6
<211> LENGTH: 79
<212> TYPE: PRT
<213> ORGANISM: Artificial Sequence
<220> FEATURE:
<223> OTHER INFORMATION: synthetic IGF1 R50E mutant with C-terminal
      6His-tag

<400> SEQUENCE: 6

Met Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr Gly Tyr
            20                  25                  30

Gly Ser Ser Ser Arg Arg Ala Pro Gln Thr Gly Ile Val Asp Glu Cys
        35                  40                  45

Cys Phe Glu Ser Cys Asp Leu Arg Arg Leu Glu Met Tyr Cys Ala Pro
    50                  55                  60

```
Leu Lys Pro Ala Lys Ser Ala Leu Glu His His His His His
 65                  70                  75
```

```
<210> SEQ ID NO 7
<211> LENGTH: 153
<212> TYPE: PRT
<213> ORGANISM: Homo sapiens
<220> FEATURE:
<223> OTHER INFORMATION: human wild type insulin-like growth factor 1
      (IGF1, IGF-1A, IGFBP1), somatomedin-C, mechano
      growth factor (MGF) precursor

<400> SEQUENCE: 7
```

```
Met Gly Lys Ile Ser Ser Leu Pro Thr Gln Leu Phe Lys Cys Cys Phe
 1               5                  10                  15

Cys Asp Phe Leu Lys Val Lys Met His Thr Met Ser Ser Ser His Leu
             20                  25                  30

Phe Tyr Leu Ala Leu Cys Leu Leu Thr Phe Thr Ser Ser Ala Thr Ala
         35                  40                  45

Gly Pro Glu Thr Leu Cys Gly Ala Glu Leu Val Asp Ala Leu Gln Phe
     50                  55                  60

Val Cys Gly Asp Arg Gly Phe Tyr Phe Asn Lys Pro Thr Gly Tyr Gly
 65                  70                  75                  80

Ser Ser Ser Arg Arg Ala Pro Gln Thr Gly Ile Val Asp Glu Cys Cys
                 85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150
```

```
<210> SEQ ID NO 8
<211> LENGTH: 1076
<212> TYPE: DNA
<213> ORGANISM: Homo sapiens
<220> FEATURE:
<223> OTHER INFORMATION: human wild type insulin-like growth factor 1
      (IGF1, IGF-1A, IGFBP1), somatomedin-C, mechano
      growth factor (MGF) precursor cDNA
<220> FEATURE:
<221> NAME/KEY: CDS
<222> LOCATION: (149)..(610)
<223> OTHER INFORMATION: IGF1

<400> SEQUENCE: 8
```

```
ttcagagcag atagagcctg cgcaatggaa taaagtcctc aaaattgaaa tgtgacattg    60
ctctcaacat ctcccatctc tctggatttc tttttgcttc attattcctg ctaaccaatt   120
cattttcaga ctttgtactt cagaagcaat gggaaaaatc agcagtcttc aacccaatt    180 atttaagtgc tgcttttgtg atttcttgaa ggtgaagatg cacaccatgt cctcctcgca   240
tctcttctac ctggcgctgt gcctgctcac cttcaccagc tctgccacgg ctggaccgga   300
gacgctctgc ggggctgagc tggtggatgc tcttcagttc gtgtgtggag acaggggctt   360
ttatttcaac aagcccacag ggtatggctc agcagtcgg agggcgcctc agacaggcat   420
cgtggatgag tgctgcttcc ggagctgtga tctaaggagg ctggagatgt attgcgcacc   480
cctcaagcct gccaagtcag ctcgctctgt ccgtgcccag cgccacaccg acatgccaa   540 gacccagaag gaagtacatt tgaagaacgc aagtagaggg agtgcaggaa acaagaacta   600
```

```
caggatgtag gaagaccctc ctgaggagtg aagagtgaca tgccaccgca ggatcctttg      660
ctctgcacga gttacctgtt aaactttgga acacctacca aaaataagt ttgataacat       720 ttaaaagatg ggcgtttccc ccaatgaaat acacaagtaa acttccaaca ttgtctttag      780
gagtgatttg caccttgcaa aaatggtcct ggagttggta gattgctgtt gatcttttat      840
caataatgtt ctatagaaaa gaaaaaaaaa attatatata tatatatatc ttagtccctg      900
cctctcaaga gccacaaatg catgggtgtt gtatagatcc agttgcacta aattcctctc      960
tgaatcttgg ctgctggagc cattcattca gcaaccttgt ctaagtggtt tatgaattgt     1020
ttccttattt gcacttcttt ctacacaact cgggctgttt gttttacagt gtctga         1076
```

<210> SEQ ID NO 9
<211> LENGTH: 6
<212> TYPE: PRT
<213> ORGANISM: Artificial Sequence
<220> FEATURE:
<223> OTHER INFORMATION: synthetic C-terminal 6His-tag

<400> SEQUENCE: 9

```
His His His His His His
 1               5
```

<210> SEQ ID NO 10
<211> LENGTH: 7
<212> TYPE: PRT
<213> ORGANISM: Artificial Sequence
<220> FEATURE:
<223> OTHER INFORMATION: synthetic beta1 integrin specificity loop
      sequence critical for ligand specificity of avbeta1
      integrin, beta1 integrin residues 187-193

<400> SEQUENCE: 10

```
Cys Thr Ser Glu Gln Asn Cys
 1               5
```

<210> SEQ ID NO 11
<211> LENGTH: 8
<212> TYPE: PRT
<213> ORGANISM: Artificial Sequence
<220> FEATURE:
<223> OTHER INFORMATION: synthetic beta3 integrin specificity loop
      sequence critical for ligand specificity of avbeta3
      integrin, beta3 integrin residues 177-193

<400> SEQUENCE: 11

```
Cys Tyr Asp Met Lys Thr Thr Cys
 1               5
```